(12) United States Patent
Pic et al.

(10) Patent No.: US 12,226,793 B2
(45) Date of Patent: Feb. 18, 2025

(54) FLUIDIZATION DEVICES AND METHODS OF USE

(71) Applicant: Boston Scientific Scimed, Inc., Maple Grove, MN (US)

(72) Inventors: Andrew Pic, Northboro, MA (US); Joseph King, Franklin, MA (US); Amanda Smith, Boston, MA (US); Jessica Grimsby, Watertown, MA (US); John Favreau, Spencer, MA (US); Lauren Lydecker, Millbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/496,982

(22) Filed: Oct. 30, 2023

(65) Prior Publication Data

US 2024/0050968 A1   Feb. 15, 2024

Related U.S. Application Data

(63) Continuation of application No. 16/589,554, filed on Oct. 1, 2019, now Pat. No. 11,833,539.
(Continued)

(51) Int. Cl.
*B05B 7/14* (2006.01)
*A61M 11/02* (2006.01)
(Continued)

(52) U.S. Cl.
CPC .......... *B05B 7/1463* (2013.01); *A61M 11/02* (2013.01); *A61M 13/00* (2013.01);
(Continued)

(58) Field of Classification Search
CPC .... B05B 7/1463; B05B 7/1413; A61M 11/02; A61M 13/00; A61M 15/0008;
(Continued)

(56) References Cited

U.S. PATENT DOCUMENTS

| 471,854 A | 3/1892 | Howard |
|---|---|---|
| 881,238 A | 3/1908 | Hasbrouck |

(Continued)

FOREIGN PATENT DOCUMENTS

| CN | 102264406 A | 11/2011 |
|---|---|---|
| CN | 101401956 B | 11/2012 |

(Continued)

OTHER PUBLICATIONS

Japanese Notice of Allowance in corresponding Japanese Application No. 2021-517012, dated Feb. 7, 2024 (6 pages).
(Continued)

*Primary Examiner* — Kendra D Carter
*Assistant Examiner* — Arielle Wolff
(74) *Attorney, Agent, or Firm* — Bookoff McAndrews, PLLC

(57) ABSTRACT

A device for fluidizing and delivering a powdered agent, including a canister extending longitudinally from a first to a second end and defining a space within which a powdered agent is received, an inlet coupleable to a gas source for supplying gas to the space to fluidize the powdered agent to create a fluidized mixture, an outlet via which the gas mixture is delivered to a target area, a tube extending from the outlet into the interior space, the tube including a slot extending through a wall thereof so that gas mixture is passable from the interior space through the outlet via the second end and the slot, and a door movably coupled to the tube so that the door is movable over the slot to control a size of the slot open to the interior space of the canister.

20 Claims, 11 Drawing Sheets

Related U.S. Application Data

(60) Provisional application No. 62/740,242, filed on Oct. 2, 2018, provisional application No. 62/747,863, filed on Oct. 19, 2018.

(51) Int. Cl.
  *A61M 13/00* (2006.01)
  *A61M 15/00* (2006.01)

(52) U.S. Cl.
  CPC .... *A61M 15/0008* (2014.02); *A61M 15/0086* (2013.01); *A61M 2202/064* (2013.01)

(58) Field of Classification Search
  CPC ........ A61M 15/0086; A61M 2202/064; A61M 2205/10; A61M 2206/16; A61M 15/0005; A61M 2205/3334; A61M 31/00; A61M 2205/8225; A61M 11/006; A61M 11/007; A61M 11/008; A61M 2202/0007; A61B 17/00491; A61B 2017/00522
  See application file for complete search history.

(56) References Cited

U.S. PATENT DOCUMENTS

| | | | |
|---|---|---|---|
| 1,145,520 A | 7/1915 | Smith |
| 1,599,959 A | 9/1926 | Buheiji |
| 1,732,566 A | 10/1929 | McKendrick |
| 2,151,418 A | 3/1939 | Bolté |
| 2,185,927 A | 6/1940 | Shelanski |
| 2,478,715 A | 8/1949 | Schmitt |
| 2,623,519 A | 12/1952 | Cohen |
| 3,669,113 A | 6/1972 | Altounyan et al. |
| 3,940,061 A | 2/1976 | Gimple et al. |
| 4,067,499 A | 1/1978 | Cohen |
| 4,184,258 A | 6/1980 | Barrington et al. |
| 4,427,450 A | 1/1984 | Kostansek |
| 4,457,329 A | 7/1984 | Werley et al. |
| 4,806,167 A | 2/1989 | Raythatha |
| 5,215,221 A | 6/1993 | Dirksing |
| 5,231,983 A | 8/1993 | Matson et al. |
| 5,273,531 A | 12/1993 | Knoepfler |
| 5,312,331 A | 5/1994 | Kneopfler |
| 5,312,333 A | 5/1994 | Churinetz et al. |
| 5,366,122 A | 11/1994 | Guentert et al. |
| 5,445,612 A | 8/1995 | Terakura et al. |
| 5,470,311 A | 11/1995 | Setterstrom et al. |
| 5,884,621 A | 3/1999 | Matsugi et al. |
| 5,951,531 A | 9/1999 | Ferdman et al. |
| 6,003,512 A | 12/1999 | Gerde |
| 6,447,816 B1 | 9/2002 | Vail, III et al. |
| 6,484,750 B1 | 11/2002 | Foos et al. |
| 6,551,302 B1 | 4/2003 | Rosinko et al. |
| 6,554,022 B2 | 4/2003 | Wakeman |
| 6,589,087 B2 | 7/2003 | Mackal et al. |
| 6,684,917 B2 | 2/2004 | Zhu et al. |
| 6,708,712 B2 | 3/2004 | Wakeman |
| 6,716,190 B1 | 4/2004 | Glines et al. |
| 6,799,571 B1 | 10/2004 | Hughes et al. |
| 7,178,547 B2 | 2/2007 | Mackal |
| 7,311,270 B2 | 12/2007 | Kapila |
| 7,334,598 B1 | 2/2008 | Hollars |
| 7,361,300 B2 | 4/2008 | Kelly et al. |
| 7,427,607 B2 | 9/2008 | Suzuki |
| 7,455,248 B2 | 11/2008 | Kablik et al. |
| 7,461,649 B2 | 12/2008 | Gamard et al. |
| 7,544,177 B2 | 6/2009 | Gertner |
| 7,563,299 B2 | 7/2009 | Baptista da Costa et al. |
| 7,673,647 B2 | 3/2010 | Mackal |
| 7,841,338 B2 | 11/2010 | Dunne et al. |
| 7,892,205 B2 | 2/2011 | Palasis et al. |
| 7,921,874 B2 | 4/2011 | Tekulve et al. |
| 8,037,880 B2 | 10/2011 | Zhu et al. |
| 8,097,071 B2 | 1/2012 | Burgess et al. |
| 8,118,777 B2 | 2/2012 | Ducharme et al. |
| 8,269,058 B2 | 9/2012 | McCarthy et al. |
| 8,313,474 B2 | 11/2012 | Campbell et al. |
| 8,360,276 B2 | 1/2013 | Rogier et al. |
| 8,361,054 B2 | 1/2013 | Ducharme et al. |
| 8,496,189 B2 | 7/2013 | Lomond et al. |
| 8,673,065 B2 | 3/2014 | Burgess et al. |
| 8,721,582 B2 | 5/2014 | Ji |
| 8,728,032 B2 | 5/2014 | Ducharme et al. |
| 8,741,335 B2 | 6/2014 | McCarthy |
| 8,827,980 B2 | 9/2014 | Ji |
| 8,910,627 B2 | 12/2014 | Iwatschenko et al. |
| 8,951,565 B2 | 2/2015 | McCarthy |
| 9,028,437 B2 | 5/2015 | Ott et al. |
| 9,067,011 B2 | 6/2015 | Zou et al. |
| 9,089,658 B2 | 7/2015 | Dunne et al. |
| 9,101,744 B2 | 8/2015 | Ducharme |
| 9,107,668 B2 | 8/2015 | Melsheimer et al. |
| 9,132,206 B2 | 9/2015 | McCarthy |
| 9,204,957 B2 | 12/2015 | Gregory et al. |
| 9,205,170 B2 | 12/2015 | Lucchesi et al. |
| 9,205,207 B2 | 12/2015 | Ji |
| 9,205,240 B2 | 12/2015 | Greenhalgh et al. |
| 9,308,584 B2 | 4/2016 | Burgess et al. |
| 9,310,812 B2 | 4/2016 | Costle et al. |
| 9,375,533 B2 | 6/2016 | Ducharme et al. |
| 9,492,646 B2 | 11/2016 | Hoogenakker et al. |
| 9,517,976 B2 | 12/2016 | Macka |
| 9,545,490 B2 | 1/2017 | Iwatschenko et al. |
| 9,555,185 B2 | 1/2017 | Foster et al. |
| 9,629,966 B2 | 4/2017 | Ji |
| 9,636,470 B2 | 5/2017 | Pohlmann et al. |
| 9,707,359 B2 | 7/2017 | Kubo |
| 9,713,682 B2 | 7/2017 | Eistetter et al. |
| 9,717,897 B2 | 8/2017 | Rogier |
| 9,821,084 B2 | 11/2017 | Diegelmann et al. |
| 9,839,772 B2 | 12/2017 | Ducharme |
| 9,839,774 B2 | 12/2017 | Bonaldo |
| 9,846,439 B2 | 12/2017 | Carman et al. |
| 9,867,931 B2 | 1/2018 | Gittard |
| 9,976,660 B2 | 5/2018 | Stanton et al. |
| 10,004,690 B2 | 6/2018 | Lee et al. |
| 10,010,705 B2 | 7/2018 | Greenhalgh et al. |
| 10,017,231 B2 | 7/2018 | Fawcett, Jr. |
| 10,036,617 B2 | 7/2018 | Mackal |
| 10,065,004 B2 | 9/2018 | Eder et al. |
| 10,173,019 B2 | 1/2019 | Kaufmann et al. |
| 10,384,049 B2 | 8/2019 | Stanton et al. |
| 10,463,811 B2 | 11/2019 | Lee et al. |
| 10,507,293 B2 | 12/2019 | Goodman et al. |
| 10,646,706 B2 | 5/2020 | Rogier |
| 10,730,595 B2 | 8/2020 | Fawcett |
| 10,751,523 B2 | 8/2020 | Rogier |
| 10,806,853 B2 | 10/2020 | Gittard |
| 10,850,814 B2 | 12/2020 | Fawcett |
| 10,994,818 B2 | 5/2021 | Hernandez |
| 2004/0107963 A1 | 6/2004 | Finlay et al. |
| 2004/0182387 A1 | 9/2004 | Steiner et al. |
| 2004/0249359 A1 | 12/2004 | Palasis et al. |
| 2005/0056275 A1 | 3/2005 | Ingle et al. |
| 2005/0121025 A1 | 6/2005 | Gamard et al. |
| 2005/0147656 A1 | 7/2005 | McCarthy et al. |
| 2005/0205087 A1 | 9/2005 | Kablik et al. |
| 2005/0220721 A1 | 10/2005 | Kablik et al. |
| 2006/0004314 A1 | 1/2006 | McCarthy et al. |
| 2006/0100587 A1 | 5/2006 | Bertron et al. |
| 2006/0213514 A1 | 9/2006 | Price et al. |
| 2007/0056586 A1 | 3/2007 | Price et al. |
| 2007/0066920 A1 | 3/2007 | Hopman et al. |
| 2007/0066924 A1 | 3/2007 | Hopman et al. |
| 2007/0082023 A1 | 4/2007 | Hopman et al. |
| 2007/0125375 A1 | 6/2007 | Finlay et al. |
| 2007/0151560 A1 | 7/2007 | Price et al. |
| 2007/0083137 A1 | 8/2007 | Hopman et al. |
| 2007/0199824 A1 | 8/2007 | Hoerr et al. |
| 2008/0021374 A1 | 1/2008 | Kawata |
| 2008/0141991 A1 | 6/2008 | Liu |
| 2008/0287907 A1 | 11/2008 | Gregory et al. |
| 2009/0101144 A1 | 4/2009 | Gamard et al. |
| 2009/0155342 A1 | 6/2009 | Diegemann et al. |

(56) References Cited

U.S. PATENT DOCUMENTS

| | | | |
|---|---|---|---|
| 2009/0281486 A1* | 11/2009 | Ducharme | A61M 5/16881 604/147 |
| 2010/0121261 A1 | 5/2010 | Kablik et al. | |
| 2010/0160897 A1 | 6/2010 | Ducharme et al. | |
| 2010/0305505 A1 | 12/2010 | Ducharme et al. | |
| 2010/0326438 A1 | 12/2010 | Dunne | |
| 2011/0073200 A1 | 3/2011 | Overvaag et al. | |
| 2011/0178495 A1 | 7/2011 | Ji | |
| 2011/0274726 A1 | 11/2011 | Guo et al. | |
| 2011/0308516 A1 | 12/2011 | Price et al. | |
| 2012/0029354 A1 | 2/2012 | Mark et al. | |
| 2014/0116435 A1 | 5/2014 | Zierenberg | |
| 2014/0203098 A1 | 7/2014 | Bierie | |
| 2014/0271491 A1 | 9/2014 | Gittard et al. | |
| 2014/0364837 A1* | 12/2014 | Boyes | A61M 15/08 604/514 |
| 2015/0094649 A1 | 4/2015 | Gittard | |
| 2015/0125513 A1 | 5/2015 | McCarthy | |
| 2016/0074579 A1 | 3/2016 | Ilan et al. | |
| 2016/0375202 A1* | 12/2016 | Goodman | A61L 26/0023 |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |
| 2019/0134366 A1 | 5/2019 | Erez et al. | |
| 2019/0217315 A1 | 7/2019 | Maguire et al. | |
| 2019/0232030 A1 | 8/2019 | Pic et al. | |
| 2021/0024187 A1 | 1/2021 | Fawcett et al. | |
| 2021/0069485 A1 | 3/2021 | Rogier | |

FOREIGN PATENT DOCUMENTS

| | | |
|---|---|---|
| CN | 103974635 A | 8/2014 |
| DE | 60215438 T2 | 8/2007 |
| EP | 2957312 A1 | 12/2015 |
| EP | 3052168 B1 | 11/2019 |
| EP | 3313485 B1 | 7/2020 |
| FR | 2863503 A1 | 6/2005 |
| JP | H07118305 A | 5/1995 |
| JP | 2007-503930 A | 3/2007 |
| JP | 2011-519679 A | 7/2011 |
| JP | 2018-518310 A | 7/2018 |
| WO | 98/43894 A1 | 8/1997 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2009061409 A1 | 5/2009 |
| WO | 2013083636 A1 | 6/2013 |
| WO | 2015050814 A1 | 4/2015 |
| WO | 2018157772 A1 | 9/2018 |

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

Retsch GmbH Haan. Sieve Analysis: Taking a Close Look at Quality, an Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

Chinese Office Action issued on Jun. 22, 2022, in counterpart Chinese Patent Application No. 201980079149.4 (8 pages).

Extended European search report in corresponding European Application No. 22210075.2, dated Apr. 3, 2023 (18 pages).

* cited by examiner

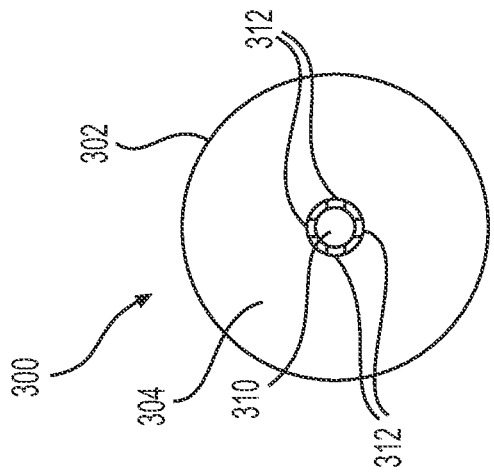
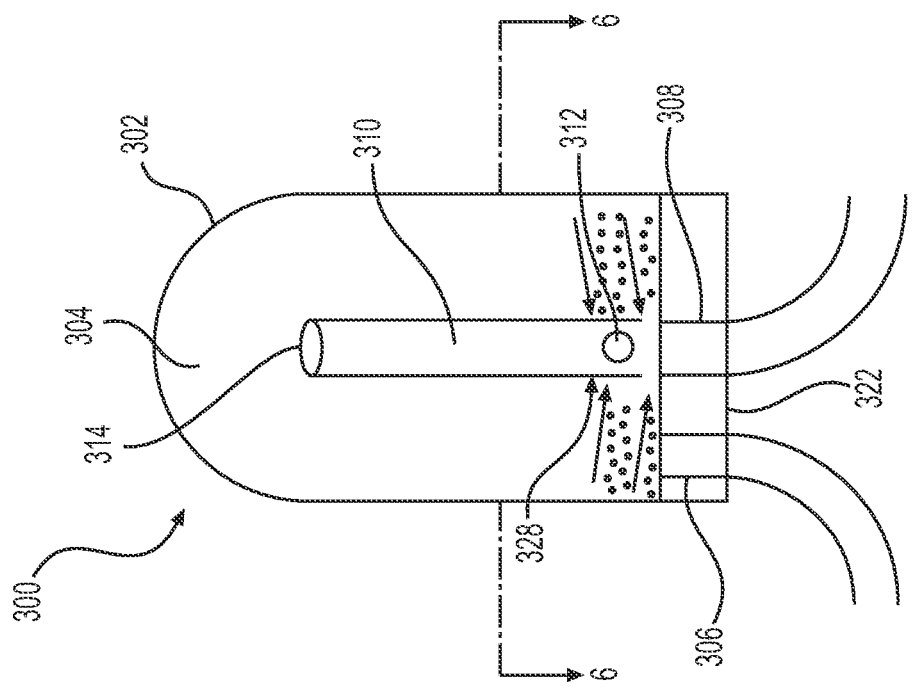

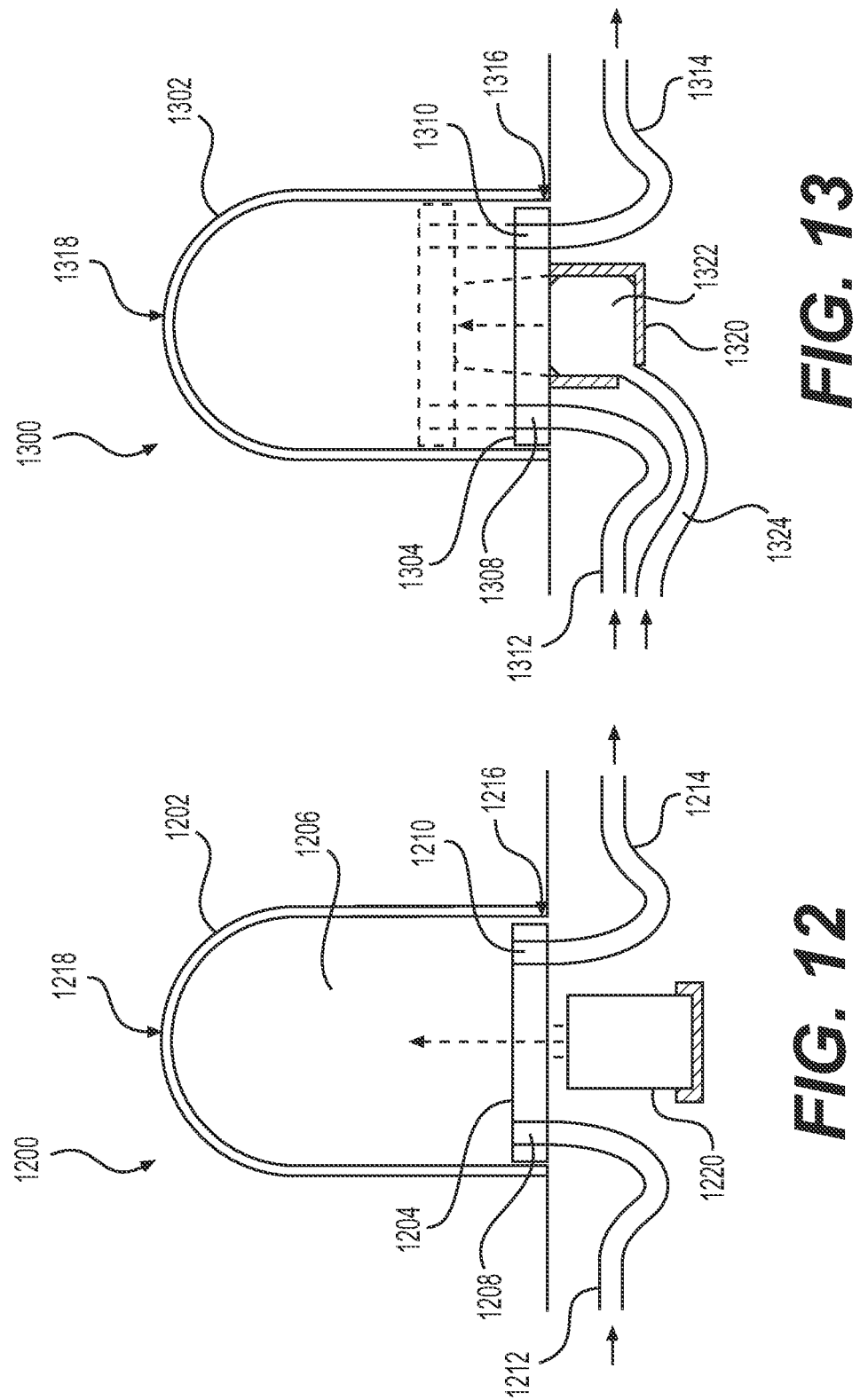

FLUIDIZATION DEVICES AND METHODS OF USE

CROSS-REFERENCE TO RELATED APPLICATIONS

This application is a continuation of U.S. patent application Ser. No. 16/589,554, filed on Oct. 1, 2019, which claims the benefit of priority from U.S. Provisional Application No. 62/740,242, filed on Oct. 2, 2018, and U.S. Provisional Application No. 62/747,863, filed on Oct. 19, 2018, each of which is incorporated by reference herein in its entirety.

TECHNICAL FIELD

The present disclosure relates generally to endoscopic medical devices and methods of use. More particularly, in some embodiments, the disclosure relates to devices and methods for fluidization of materials, e.g., powders or reagents, for dispensing the materials to a target site in a patient.

BACKGROUND

Therapeutic agents in the form of dry powders such as, for example, hemostatic agents, may be delivered to a target site within a living body using a fluidization and delivery device. Such devices have generally included a chamber in which powder is received and introduced to high flow gases to create a fluidized bed. This creates a two-phase mixture containing particulate solids suspended in gas. The suspension retains the properties of the gaseous fluid and will move in a direction from high to low pressure, effectively delivering the particulate to the lower pressure region. Hemostatic powder, for example, can be delivered to a target location (e.g., a bleeding site) through an endoscopic catheter using this method. Studies have shown that when a particulate delivery rate of hemostatic powder to the bleeding location falls below a threshold level may, in some cases, be no longer effective in achieving initial hemostasis. Current powder fluidization and delivery devices, however, often show a decrease in powder delivery rate over time.

SUMMARY OF THE DISCLOSURE

The present embodiments are directed to a device for fluidizing and delivering a powdered agent, comprising a canister extending longitudinally from a first end to a second end and defining an interior space within which a powdered agent is received, an inlet coupleable to a gas source for supplying gas to the interior space to fluidize the powdered agent received therewithin to create a fluidized mixture, an outlet via which the gas mixture is delivered to a target area for treatment, a tube extending from a first end in communication with the outlet to a second end extending into the interior space, the tube including a slot extending through a wall thereof so that gas mixture is passable from the interior space through the outlet via the second end and the slot, and a door movably coupled to the tube so that the door is movable over the slot to control a size of the slot open to the interior space of the canister.

In an embodiment, the door may be configured as an overtube movably mounted over the tube.

In an embodiment, the device may further comprise a stabilizing ring extending radially outward from the overtube to an interior surface of the canister to fix the tube relative to the canister.

In an embodiment, the canister may be rotatable relative to the tube to move the overtube longitudinally relative to the tube and control the size of the slot open to the interior space.

In an embodiment, the device may further comprise a lid coupleable to the canister to enclose the interior space, the inlet and the outlet configured as openings extending through the lid.

In an embodiment, the device may further comprise a delivery catheter coupleable to the outlet, the delivery catheter sized and shaped to be inserted through a working channel of an endoscope to the target area.

The present embodiments are also directed to a device for fluidizing and delivering a powdered agent, comprising a canister extending longitudinally from a first end to a second end and including a first interior space within which a powdered agent is received, a first inlet coupleable to a gas source for supplying gas to the interior space to fluidize the powdered agent received therewithin to create a fluidized mixture, an outlet via which the gas mixture is delivered to a target area for treatment from the first interior space, and a filler chamber in communication with the first interior space via a filler inlet, the filler chamber containing a filler material passable from the filler chamber to the first interior space to maintain a substantially constant volume of material therein, wherein the material includes at least one of the powdered agent and the filler material.

In an embodiment, the filler material may include one of mock particles, beads, bounce balls, and a foam material.

In an embodiment, the filler material may be sized, shaped and configured so that the filler material cannot be passed through the outlet.

In an embodiment, the filler chamber may be supplied with a gas to drive the filler material from the filler chamber into the first interior space.

In an embodiment, the filler chamber may be configured as a second interior space defined via the canister.

In an embodiment, the second interior space may include an angled surface directing the filler material to the filler inlet.

In an embodiment, the filler material may be additional powdered agent.

In an embodiment, the device may further comprise a door movable relative to the filler inlet between a first configuration, in which the door covers the filler inlet, to a second position, in which the door opens the filler inlet to permit filler material to pass therethrough from the filler chamber to the first interior space via gravity.

In an embodiment, the device may further comprise a turbine connected to a paddle housed within the filler inlet, the turbine driven by a flow of gas so that, when a flow of gas is received within a flow path housing the turbine, the turbine rotates to correspondingly rotate the paddle so that filler material within the filler chamber is actively driven therefrom and into the first interior space.

The present embodiments are also directed to a method, comprising supplying a gas to an interior space within a canister within which a powdered agent is received to fluidize the powdered agent, forming a fluidized mixture and delivering the fluidized mixture to a target area within a patient body via a delivery catheter inserted through a working channel of an endoscope to the target area, wherein during delivery of the fluidized mixture, a door movably mounted over the tube is moved relative to a slot extending through a wall of a tube extending into the interior space of the canister in communication with the delivery catheter, to control a size or a portion of the slot exposed to the interior space.

The present embodiments are also directed to a device for fluidizing and delivering a powdered agent, comprising a canister extending longitudinally from a first end to a second end and defining an interior space within which a powdered agent is received, an inlet coupleable to a gas source for supplying gas to the interior space to fluidize the powdered agent received therewithin to create a fluidized mixture, an outlet via which the gas mixture is delivered to a target area for treatment, and a piston movably coupled to the canister, the piston movable from an initial configuration, in which the piston is coupled to the first end of the canister, toward the second end of the canister to reduce a volume of the interior space as a volume of the powdered agent is reduced during delivery of the fluidized mixture to the target area.

In an embodiment, each of the inlet and the outlet may extend through a portion of the piston.

In an embodiment, the outlet may be coupleable to a delivery catheter sized and shaped to be inserted through a working channel of an endoscope to the target area.

In an embodiment, the piston may be movable via one of a pneumatic cylinder and motor.

In an embodiment, the device may further comprise a chamber connected to the first end on the canister on a side of the piston opposing the interior space of the canister, the chamber housing an expandable member which is configured to receive gas during delivery of the fluidized mixture so that the expandable mixture expands to move the piston toward the second end of the canister.

In an embodiment, the expandable member may be configured to be connected to the gas source via a connecting member including a one way valve which permits a flow of gas into the expandable member while preventing a flow of gas out of the expandable member.

In an embodiment, the device may further comprise a bypass connected to the first end of the canister and coupled to the piston via a threaded rod, the bypass housing a turbine connected to the threaded rod and being configured to receive a flow of gas therethrough so that, when gas flows through the bypass during delivery of the fluidized mixture, the turbine and threaded rod rotate to move the piston toward the second end of the canister.

The present embodiments are directed to a device for fluidizing and delivering a powdered agent, comprising a canister extending longitudinally from a first end to a second end and including a first interior space within which a powdered agent is received, an inlet coupleable to a gas source for supplying gas to the interior space to fluidize the powdered agent received therewithin to create a fluidized mixture, an outlet via which the gas mixture is delivered to a target area for treatment, and an expandable member movable between an initial biased configuration and an expanded configuration in which the expandable member is deformed so that a portion of the expandable member extends into the first interior space to reduce a volume thereof as a volume of the powdered agent therein is reduced during delivery of the fluidized mixture to the target area.

In an embodiment, the canister may further include a second interior space configured to receive a gas therein during delivery of the fluidized mixture to the target area.

In an embodiment, the first and second interior spaces may be separated from one another via an expandable member, a pressure differential between the first and second interior spaces causing the expandable member to deform into the first interior space.

In an embodiment, the expandable member may be a diaphragm.

In an embodiment, the first interior space may be defined via an interior wall of the expandable member and the second interior space may be defined via an exterior wall of the expandable member and an interior surface of the canister.

In an embodiment, the expandable member may be substantially cylindrically shaped.

In an embodiment, the expandable member may extend from the first end of the canister to the second end of the canister.

In an embodiment, the expandable member may be a balloon housed within the canister and configured to receive a gas therewithin so that, as the balloon is inflated, the balloon fills the first interior space.

The present embodiments are also directed to a method, comprising supplying a gas to an interior space within a canister within which a powdered agent is received to fluidize the powdered agent, forming a fluidized mixture, and delivering the fluidized mixture to a target area within a patient body via a delivery catheter inserted through a working channel of an endoscope to the target area, wherein during delivery of the fluidized mixture, a volume of the interior space of the canister is reduced to correspond to a reduction in volume of the powdered agent so that a rate of delivery of the fluidized mixture remains substantially constant.

BRIEF DESCRIPTION OF THE DRAWINGS

The accompanying drawings, which are incorporated in and constitute a part of this specification, illustrate various embodiments and together with the description, serve to explain the principles of the disclosed embodiments.

FIG. 5 shows a schematic view of a device according to yet another embodiment of the present disclosure;

FIG. 6 shows a lateral cross-sectional view of the device of FIG. 5 along the line 6-6;

FIG. 12 shows a schematic view of a device according to an embodiment of the present disclosure;

FIG. 13 shows a schematic view of a device according to an alternate embodiment of the present disclosure;

DETAILED DESCRIPTION

Figure 2:
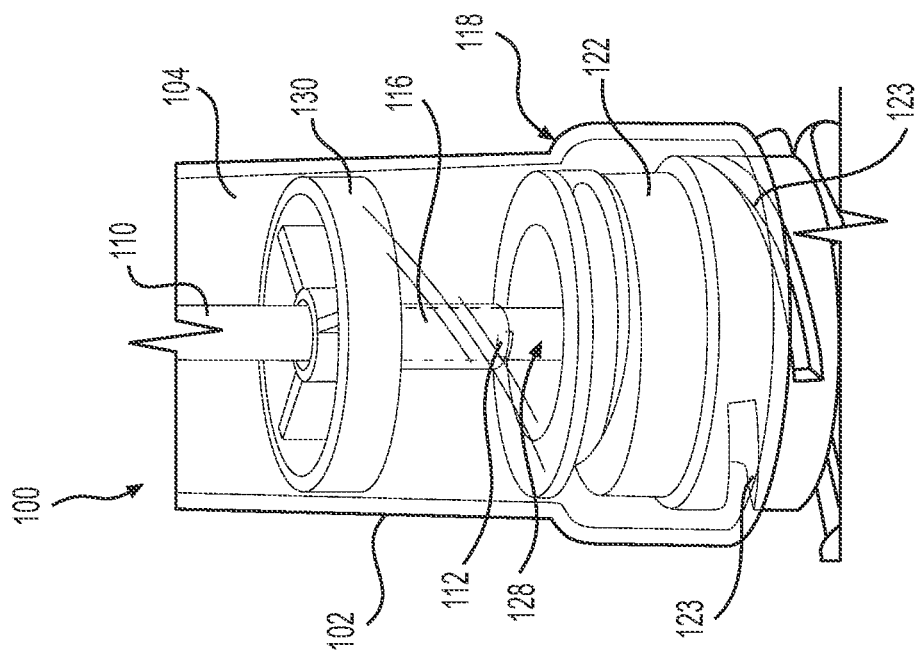
FIG. 2 shows a perspective view of the device of FIG. 1, in a second configuration.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

The present disclosure may be further understood with reference to the following description and the appended drawings, wherein like elements are referred to with the same reference numerals. The present disclosure relates to devices and methods for delivering fluidized powder at a constant delivery rate to increase a duration of a period during which an effective rate of delivery of the powdered agent may be maintained allowing a user (e.g., a physician) to treat more bleeding areas without having the delivery rate of the powder fall below the threshold rate required to achieve hemostasis. This can reduce the number of devices needed per procedure (and/or the number of times a device needs to be reloaded or reset) thereby reducing treatment time. In one embodiment, a device includes features for changing a size of a powder exit opening during delivery of the fluidized powder to maintain a desired rate of delivery over time. In another embodiment, a device includes a turbulator plate to prevent settling of powder within a canister to maintain a desired rate of delivery of the powder. In another embodiment, a device includes a plurality of powder exit slots distributed about a tube extending into a canister in which the powder is received to prevent uneven powder distribution within the canister. In yet another embodiment, a device maintains a constant volume of material within the canister to maintain a substantially constant delivery rate by injecting filler material and/or additional powder as fluidized powder is delivered. In another embodiment, a user (e.g., physician) to maintain an effective and optimal delivery zone for a longer duration of time. This would allow the user to treat more bleeding areas, reducing the number of devices needed per procedure and thereby reducing treatment time. Embodiments describe a powder fluidization chamber and delivery device which, over time, reduces an interior volume of a fluidizing canister as the powder volume is decreased during delivery. The canister volume may be reduced to maintain a powder to canister volume ratio throughout the entire procedure to maintain a constant delivery rate during the treatment. It will be understood by those of skill in the art that all of these features maintain a desired fluidized powder delivery rate during the course of treatment. For example, the desired rate of delivery may be maintained substantially constant during a period of application of the powder or the rate may fluctuate within a desired range of delivery rates without falling below a critical threshold delivery rate (e.g., a rate below which delivery of the powder is no longer effective for its intended therapeutic purpose).

Figure 1:
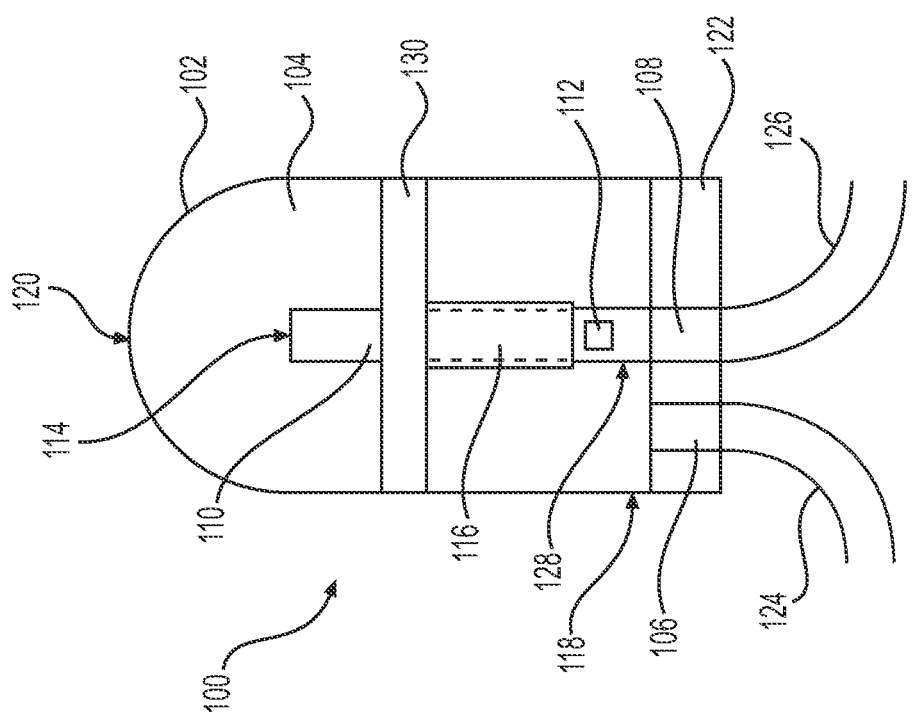
FIG. 1 shows a schematic view of a device according to a first embodiment, in a first configuration.

As shown in FIGS. 1 and 2, a device 100 for fluidizing and delivering a powdered agent (e.g., a powdered therapeutic agent) to a site within a living body (e.g., a target site) according to an embodiment of the present disclosure comprises a canister 102 configured to receive the powdered agent (e.g., hemostatic agent) within an interior space 104 thereof. Hemostatic agents may include, for example, powdered agents using granular chitosan salt, Zeolite powder, smectite clay and Poly Acrylic Acid, or polysaccharide hemospheres derived from potato starch. The device 100 includes an inlet 106 via which gas (e.g., $CO_2$) is supplied to the canister 102 to fluidize the powdered agent and form a fluidized powder mixture and an outlet 108 via which the fluidized powder mixture exits the canister 102 to be delivered to the target site (e.g., bleeding site) via, for example a flexible delivery device (e.g., an endoscope) inserted through a body lumen accessed via a natural body orifice. A tube 110 (e.g., a hypotube) extends from the outlet 108 and into the interior space 104 of the canister 102 so that the fluidized powder mixture may be received therein to exit the canister 102. The tube 110 in this embodiment includes a slot 112 extending through a wall thereof so that fluidized powder mixture may exit the canister 102 from both an end 114 of the tube 110 and through the slot 112. The device 100 according to this embodiment further comprises an overtube 116 movably mounted over a portion of the tube 110 so that the overtube 116 may be moved along a length of the tube 110 to extend over the slot 112, controlling a size of an opening of the slot 112. Testing has shown that increasing the slot size increases the powder delivery rate while decreasing the slot size decreases the powder delivery rate. The overtube 116 is movable relative to the tube 110 from an initial configuration, in which the overtube 116 at least partially covers the slot 112 toward an open configuration, in which the overtube 116 is moved along a length of the tube 110 to gradually increase the size of the slot 112 during the course of the treatment procedure so that the rate of delivery of the fluidized powder delivery may be maintained above a threshold level (e.g., be held substantially consistent over time) even as a volume of the powdered agent within the canister 102 decreases as the powder is dispensed. It will be understood that a fluidized powder/material includes, but is not limited to, a powder/material that acquires the characteristics of a fluid by passing a propellant fluid (such as a gas) with in or through it, and also an agitated powder/material which is a material that follows a propellant fluid or is pushed by a propellant fluid.

According to an embodiment, a target delivery rate may be, for example, greater than 1 gram for every 5 seconds of delivery. The device 100 may provide the best delivery results when the canister 102 is approximately 45% to 80% filled with the powdered agent. For example, at 80% fill the target rate may be sustained for 30 delivery seconds. This delivery rate is also dictated by the amount of gas that the device 100 may use for delivery. By gradually increasing the size of the slot 112 through which the fluidized powder mixture may exit the canister 102, the delivery rate may be maintained (e.g., past 30 delivery seconds) even as the volume of the powdered agent within the canister 102 decreases.

The canister 102 in this embodiment extends longitudinally from an open first end 118 to a closed second end 120 to define the interior space 104, which is configured to receive the powdered agent therein. A lid 122 is coupled to the first end 118 to enclose the interior space 104 and prevent the powdered agent and/or gas from leaking from the interior space 104. In one embodiment, the lid 122 is received within the first end 118 and coupled thereto. The inlet 106 and/or the outlet 108 in this embodiment are configured as openings extending through the lid 122. It will be understood by those of skill in the art, however, that the inlet 106 and the outlet 108 may have any of a variety of configurations so long as the inlet 106 and the outlet 108 are connectable to a gas source and a delivery member, respectively, for supplying a high flow gas to the powdered agent to fluidize the powdered agent and deliver the fluidized powder mixture to the target site. For example, the inlet 106 may be coupled to a connecting member 124 which connects the gas source to the inlet 106. In an embodiment, gas may be supplied to the canister 102 at a pressure ranging from between 5 and 20 psi and/or a flow rate of 8-15 standard liters per minute. The outlet 108 in this embodiment is coupled to a flexible delivery catheter 126 sized, shaped and configured to be inserted through a working channel of a flexible endoscope to the target site within a living body. In one example, the delivery catheter 126 may have an inner diameter between 0.065 inches and 0.11 inches. In another embodiment, the inlet 106 and the outlet 108 may extend through a portion of the canister 102.

The tube 110 extends from a first end 128 connected to the outlet 108 to a second end 114 extending into the interior space 104. As described above, the tube 110 in FIGS. 1 and 2 also includes slot 112, which extends through the wall of the tube 110. The slot 112 in this embodiment is positioned proximate the first end 128 so that the fluidized powder mixture may exit the interior space 104 of the canister 102 via one of second end 114 of the tube 110 and the slot 112 proximate the first end 128.

The overtube 116 is movably mounted over a portion of a length of the tube 110. The overtube 116 is movable relative to the tube 110 so that, as the overtube 116 moves over the tube 110, an area of the slot 112 covered by the overtube 116 is varied to control a size of a portion of the slot 112 exposed to the interior space 104 and through which the fluidized powder mixture may exit the interior space 104 of the canister 102. For example, in an initial configuration, the overtube 116 extends over the entire slot 112 so that the slot 112 is completely covered, preventing any fluidized powder mixture from exiting therethrough. During the course of treatment of the target site, however, the overtube 116 may be moved relative to the tube 110 to increase the size of the portion of the slot 112 exposed and through which the fluidized powder may exit to maintain the delivery rate of the fluidized powder mixture at a desired level (e.g., above a threshold delivery rate). For example, FIG. 2 shows the slot 112 when it is partially covered via a portion of the overtube 116 and FIG. 3 shows the slot 112 when it is entirely exposed. Although the embodiment describes an initial configuration in which the entire slot 112 is covered, it will be understood by those of skill in the art that, in an initial configuration, the overtube 116 may have any of a variety of positions relative to the slot 112, so long as the size of the slot 112, through which the fluidized powder may exit, is increased during the course of treatment as the powder in the canister 102 is dispensed.

It will also be understood by those of skill in the art that the overtube 116 may be moved relative to the tube 110 via any of a variety of mechanisms. In one embodiment, the overtube 116 may be connected to a stabilizing ring 130 which extends, for example, radially outward from the overtube 116 to an interior surface of the canister 102 to fix a position of the overtube 116 relative to the canister 102. The canister 102 and the tube 110 in this example are rotatably coupled to one another so that, when the canister 102 is rotated relative to the tube 110, the overtube 116 correspondingly rotates about the tube 110 while also moving longitudinally relative to the tube 110 to increase (or decrease, depending on the direction of rotation) a size of the slot 112 through which the fluidized powder mixture may exit. In one example, the lid 122, from which the tube 110 extends, includes cam paths 123 extending along a partially helical path, within which an engaging feature (e.g., a protrusion) of the canister 102 rides so that, as the canister 102 and, consequently, the overtube 116 are rotated relative to the lid 122 and the tube 110, the overtube 116 moves longitudinally relative to the tube 110. As would be understood by those skilled in the art, the cam paths 123 and the corresponding engaging features of the canister 102 function similarly to a threaded engagement between the canister 102 and the lid 122 to achieve the desired relative movement between the overtube 116 and the tube 110.

Although the embodiment describes the size of the portion of the slot 112 available for fluidized powder mixture to exit as controlled via the overtube 116, the size of the slot 112 may be controlled via any "door" having any of a variety of structures and geometries so long as the "door" may be gradually opened during the course of a treatment procedure to maintain a desired flow rate of therapeutic agent out of the canister 102. Movement of the overtube 116 or any other "door" may be actuated mechanically, e.g., by physically twisting the overtube 116, or may be actuated pneumatically by the flow of gas. In addition, although the embodiment shows and describes a single slot 112, the tube 110 may include more than one slot 112, which may be covered and/or exposed, as desired, via any of a number of door mechanisms, as described above.

According to an example method using the device 100, the canister 102 is filled with a powdered agent such as, for example, a hemostatic agent, prior to assembly of the device 100. Upon filling the canister 102 with a desired amount of powdered therapeutic agent, the canister 102 is assembled with the lid 122 to seal the powdered agent therein. The inlet 106 is then coupled to the gas source via, for example, the connecting member 124 and the outlet 108 is coupled to the delivery catheter 126. The delivery catheter 126 is then inserted to the target site within the living body (e.g., through a working channel of a delivery device such as, for example, an endoscope). High flow gas is introduced into the interior space 104 of the canister 102 to form the fluidized powder mixture. The user may depress a trigger or other controller to spray the fluidized mixture and to deliver the fluidized mixture to the target are (e.g., a bleeding site) to provide treatment thereto. As the fluidized powder mixture is being delivered to the target site, the user may physically rotate the canister 102 relative to the tube 110 to increase the size of the slot 112 through which the fluidized mixture is exiting the interior space 104 to maintain a desired flow level. Alternatively, if a trigger is being used to control delivery of the fluidized powder mixture, when the trigger is depressed, a pneumatic cylinder or motor may be operated to rotate and move the lid 122 relative to the canister 102 so that a larger cross-sectional area of the slot 112 is exposed, increasing the size of the slot 112 through which the fluidized mixture may exit the interior space.

Thus, as a volume of the powdered agent within the canister 102 is decreased, the cross-sectional area of the slot 112 that is exposed is increased to maintain a substantially constant delivery rate of the fluidized powder mixture. Alternatively, sensors may detect a flow rate and automatically control the opening of the slot 112 to ensure that a desired flow rate is maintained.

Figure 3:
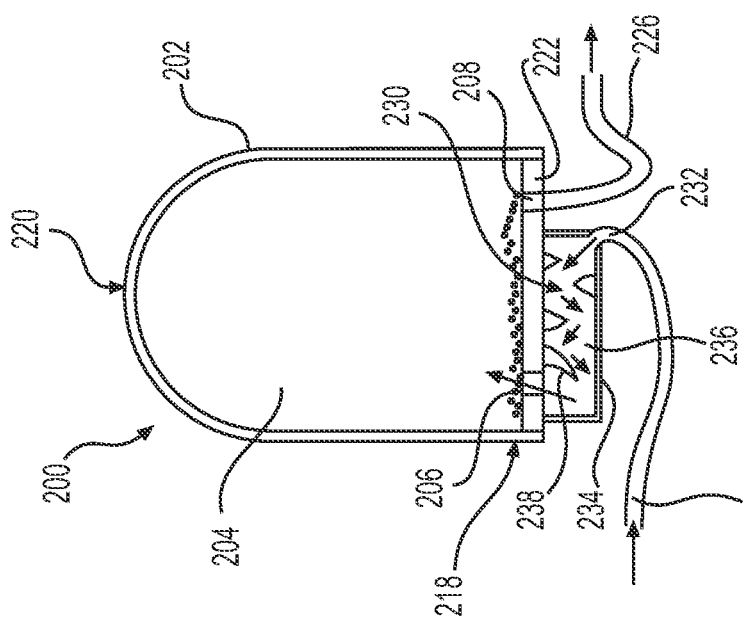
FIG. 3 shows a schematic view of a device according to another embodiment of the present disclosure.

A device 200 according to another embodiment of the present disclosure, shown in FIG. 3, is substantially similar to the device 100 as described above unless otherwise indicated. The device 200 comprises a canister 202 defining an interior space 204 within which a powdered agent is received. Similarly to the device 100, the interior space 204 is enclosed via a lid 222 coupled thereto so that the powdered agent contained within the interior space 204 forms a fluidized powder mixture when the interior space 204 is supplied with a high flow gas via an inlet 206. The fluidized powder mixture exits the interior space 204 via an outlet 208 to be delivered to a target site within a patient during treatment. To maintain a desired delivery rate as the volume of the powdered agent in the interior space 204 decreases during the course of treatment, the lid 222 includes a turbulator plate 230. As gas passes through the turbulator plate 230, the turbulator plate 230 vibrates and/or rattles to prevent, or at least reduce, settling of the powdered agent contained within the canister 202. Without the turbulator plate 230, during the course of treatment, some powdered agent would otherwise settle into an equilibrium state, resisting fluidization and making it difficult to maintain a desired delivery rate of the therapeutic agent.

Similarly to the canister 102, the canister 202 extends longitudinally from an open first end 218 to a closed second end 220 to define the interior space 204. The lid 222 is coupled to the first end 218 to enclose the interior space 204 and contain the powdered agent therein. The inlet 206 and the outlet 208 are configured as openings extending through the lid 222 in communication with the interior space 204. Although not shown, similarly to the device 100, the outlet 208 includes a tube extending therefrom and into the interior space 204 to allow the fluidized powder mixture to exit via the tube and the outlet 208.

The turbulator plate 230 in this embodiment extends along a portion of the lid 222 which faces away from the interior space 204. In this embodiment, the turbulator plate 230 includes an opening 232 extending through a wall 234 thereof, the opening 232 being configured to be connected to a gas source via, for example, a connecting element 224. The turbulator plate 230 extends along the lid 222 so that the opening 232 is in communication with the inlet 206. Thus, gas passes through the turbulator plate 230 and into the interior space 204 via the inlet 206. An interior 236 of the turbulator plate 230 includes a plurality of structures 238 such as, for example, ribs, bumps or bosses, which cause the flow of gas therethrough to be turbulent, imparting a vibratory response in the turbulator plate 230. The vibration in turn prevents the powdered agent from settling on the lid 222. Thus, the flow of gas through the turbulator plate 230 and into the interior space 204 causes both the vibration of the turbulator plate 230 and the fluidization of the powered agent within the canister 202. A magnitude of the vibration may be controlled via control of the rate at which gas is passed through the turbulator plate 230 as would be understood by those skilled in the art. In this embodiment, the magnitude of vibration of the turbulator plate 230 is held constant over time, for as long as the user is depressing a trigger to feed gas to the canister 202. The fluidized powder agent exits the canister 202 via the outlet 208, which is not in communication with the interior 236 of the turbulator plate 230. The outlet 208 in this embodiment is coupled to a delivery catheter 226 for delivering the fluidized powder mixture to the target site.

Figure 4:
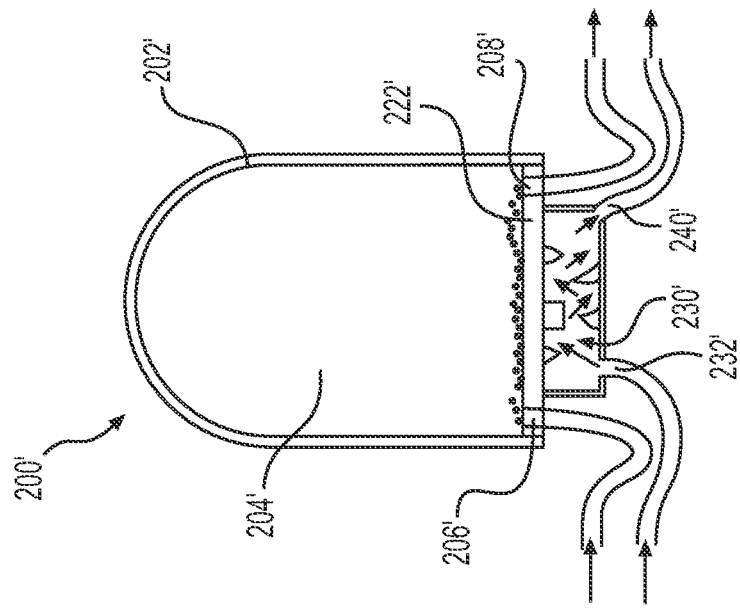
FIG. 4 shows a schematic view of a device according to an alternate embodiment of the present disclosure.

In an alternate embodiment, as shown in FIG. 4, a device 200' is substantially similar to the device 200 described above, unless otherwise indicated. In this embodiment, a turbulator plate 230' extends along a portion of a lid 222', which encloses an interior space 204' defined via a canister 202', and includes a first opening 232' and a second opening 240' extending through a wall 234' thereof. Neither the first opening 232' nor the second opening 240' are in communication with an inlet 206' and an outlet 208' of the device 200'. Each of the inlet 206' and the first opening 232' are configured to be connected to a gas source for supplying gas to the interior space 204' and the turbulator plate 230', respectively. Each of the inlet 206' and the first opening 232' is connected to the same or different gas sources.

Gas supplied to the turbulator plate 230' via the first opening 232' passes through the turbulator plate 230' and exits the turbulator plate 230' via the second opening 240'. Gas may, for example, be supplied to the turbulator plate 230' at a constant rate while the powdered agent is being fluidized and delivered to the target site to maintain a constant magnitude of vibration. Alternatively, the flow of gas supplied to the turbulator plate 230' may be changed over time, or intermittently, to change a magnitude of vibration, as desired, to optimize the rate of delivery of the fluidized powder mixture. It will be understood by those of skill in the art, however, that the function of the turbulator plate 230' remains otherwise the same as the device 200, keeping the powdered agent from settling on the lid 222'.

As shown in FIGS. 5 and 6, a device 300 according to another embodiment of the present disclosure is substantially similar to the devices 100, 200, unless otherwise indicated. The device 300 comprises a canister 302 defining an interior space 304 within which a powdered agent (e.g., hemostatic agent) is received and fluidized via a high flow gas for delivery to a target site (e.g., bleeding site) for treatment. The interior space 304 is enclosed via a lid 322 attached to an open end of the canister 302 and gas is supplied to the interior space 304 via an inlet 306 extending through the lid 322. The resulting fluidized powder mixture exits the interior space 304 via an outlet 308 extending through the lid 322 to be delivered to the target site. The device 300 also includes a tube 310 extending from a first end 328 connected to the outlet 308 to a second end 314 extending into the interior space 304. Rather than a single slot extending through a wall of the tube 310, however, the tube 310 includes a plurality of slots 312 distributed about the tube 310 to prevent uneven distribution of powder within the canister 302 and prevent powder build up on any side of the tube 310, which may decrease fluidized powder mixture delivery rates.

In one embodiment, as shown in FIG. 6, the tube 310 includes four slots 312, distributed about the tube 310 and spaced equidistantly from one another. The slots 312 in this embodiment are positioned proximate the first end 328. It will be understood by those of skill in the art, however, that the number, position and configuration of the slots 312 may be varied.

Figure 7:
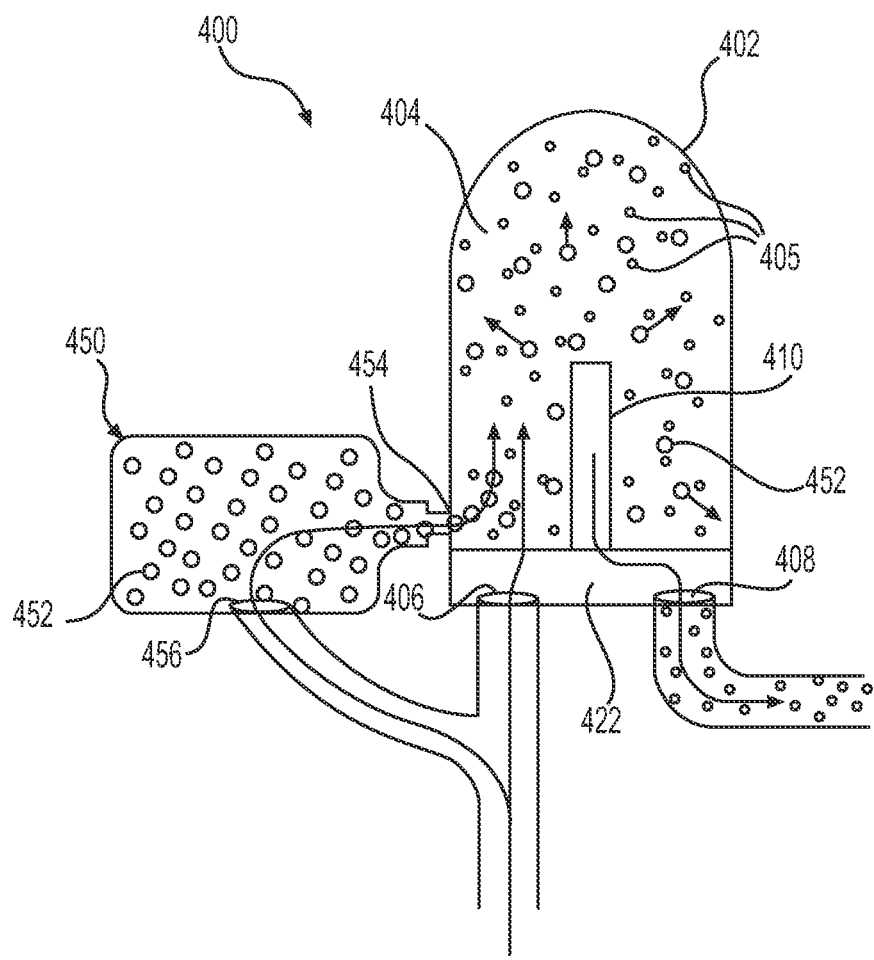
FIG. 7 shows a schematic view of a device according to another embodiment of the present disclosure.
Figure 9:
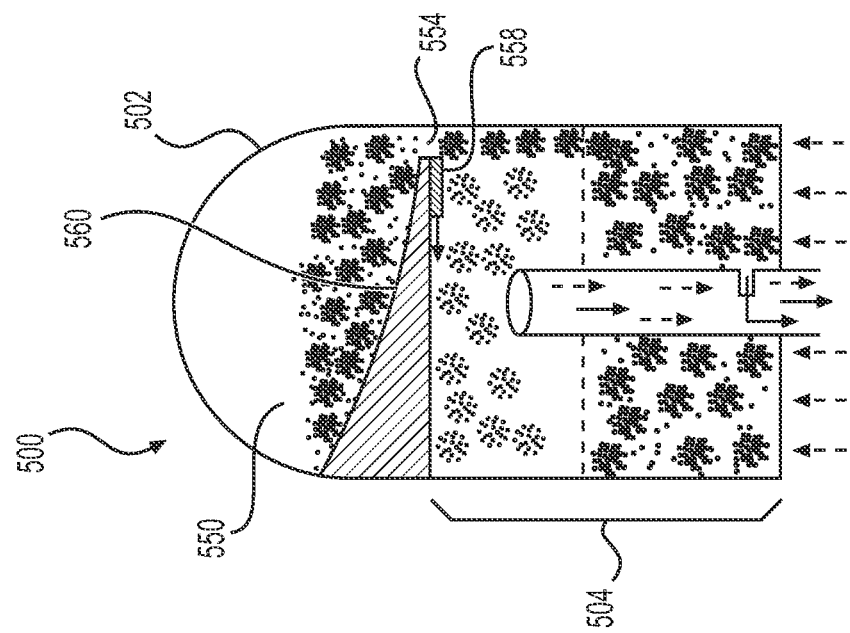
FIG. 9 shows a schematic view of the device of FIG. 8, in a second configuration.
Figure 8:
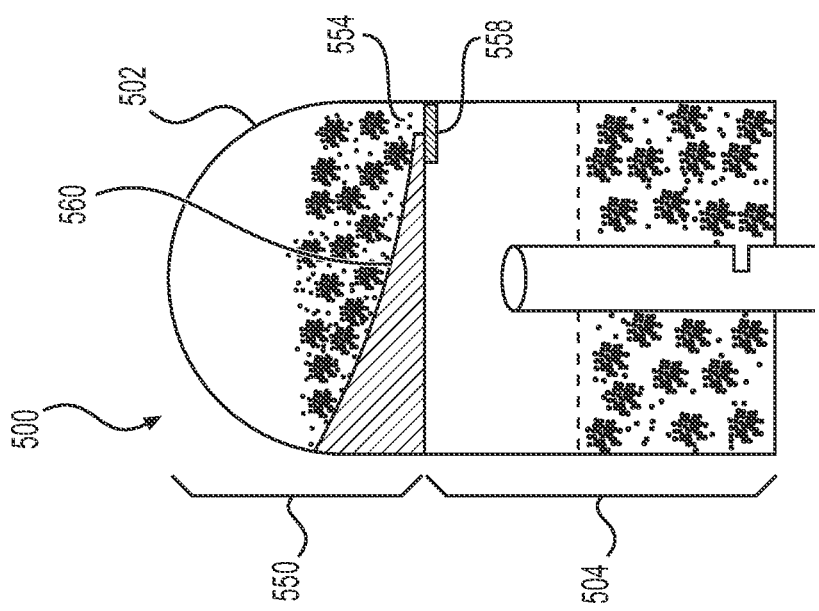
FIG. 8 shows a schematic view of a device according to yet another embodiment of the present disclosure, in a first configuration.

As shown in FIG. 7, a device 400 according to another embodiment of the present disclosure is substantially similar to the devices 100, 200, and 300 described above, unless otherwise indicated. The device 400 comprises a canister 402 defining an interior space 404 within which a powdered agent 405 is received and fluidized to form a fluidized powder mixture for delivery to a target site of within a living body. Similarly, the device 400 may include a lid 422 enclosing the interior space 404 along with an inlet 406 via which gas is supplied to the interior space 404 to fluidize the powdered agent 405 and an outlet 408 via which the fluidized powder agent exits the canister 402 to be delivered to the target site. The device 400 may also include a tube 410 extending into the interior space 404 in communication with the outlet 408. The device 400 further comprises a filler chamber 450 coupled to the canister 402, in communication with the interior space 404 of the canister 402. The filler chamber 450 houses filler material 452 such as, for example, mock particles, beads, tiny "bounce balls" or a foam material, which is injected into the canister 402 as fluidized powder mixture exits the canister 402 to make up for a loss in volume of the powdered agent as the fluidized powder mixture is delivered to the target site. The filler material 452 is injected into the canister 402 to maintain a constant ratio of volume of material (e.g., powdered agent and filler) to volume of gas within the canister 402 to maintain a desired rate of delivery of the fluidized powder mixture to the target site.

The filler chamber 450 may be connected to the canister 402 so that the filler material 452 passes from the filler chamber 450 to the canister 402 via a filler inlet 454. In one embodiment, the filler chamber 450 may also include a gas inlet 456 so that, when a user actuates the delivery of the fluidized powder mixture to the target site via, for example, pressing a trigger, gas is supplied to both the canister 402 and the filler chamber 450. The gas supplied to the filler chamber 450 drives the filler material 452 out of the filler chamber 450 into the canister 402. The filler chamber 450 may include a pressure regulator to regulate the gas inlet pressure, as necessary, to regulate the volume of filler material 452 being supplied to the canister 402 to correspond to the volume of powdered agent 405 exiting the canister 402. In one embodiment, the filler inlet 454 may be sized, shaped and/or otherwise configured to facilitate passage of a single stream of filler material 452 (e.g., beads) therethrough into the canister 402.

Filler material 452 is configured to be able to enter the interior space 404 of the canister 402, but is prevented from exiting the canister 402 during delivery of the fluidized powder mixture. In one embodiment, this is achieved via a sizing of the individual particles of the filler material 452. For example, the filler material 452 may be sized and/or shaped to prevent it from entering the tube 410 and/or the outlet 408. In other words, each bead or particle of the filler material 452 is selected to be larger than an opening of the tube 410 and/or an opening of the outlet 408. The filler material 452 is sized and shaped to be large enough to prevent the filler material from exiting the canister 402, while also being configured to bounce off walls of the canister 402 as the powdered agent is moved within the interior space 404 and is fluidized to prevent clogging of the device 400.

Thus, in use, the canister 402 of the device 400 loses powder during delivery of the fluidized powder agent, but will compensate for the loss by simultaneously supplying the canister 402 with a corresponding volume of filler material 452. The rate of delivery of filler material 452 into the canister 402 may be determined by calculating a powder volume that has been lost given a fluidized powder mixture delivery rate, and adjusting it based on volume and flow rate differences of the filler material 452 versus the powdered agent 405. The rate of delivery of filler material 452 into the canister 402 is selected to compensate for the loss in volume of the powder 405 to maintain a substantially constant fluidized powder mixture delivery rate. Although the inlet 406 of the canister 402 and the gas inlet 456 of the filler chamber 450 are shown and described as coupled to a single gas source, it will be understood by those of skill in the art that each of the inlet 406 and the gas inlet 456 may be coupled to separate gas sources, each of which supply gas to the inlet 406 and the gas inlet 456 when delivery of fluidized powder mixture to the target site is actuated and/or triggered.

As shown in FIGS. 8 and 9, a device 500 may be substantially similar to the device 400, unless otherwise indicated. The device 500 comprises a canister 502 defining a first interior space 504 within which powdered agent is received and fluidized to deliver a fluidized powder mixture to a target site of a patient for treatment. Rather than a separate filler chamber, however, the canister 502 defines both the first interior space 504 and a second interior space 550 which, when the device 500 is in an operative position, extends above the first interior space 504. In addition, rather than filling the first interior space 504 with a filler material to maintain a constant volume of material (powder and/or filler) therein, the second interior space 550 houses additional powdered agent, which may be supplied to the first interior space 504 via gravity as the fluidized powder mixture exits the first interior space 504 to be delivered to the target site. An inlet and outlet (not shown) are in communication with the first interior space 504 so that only the powdered agent contained within the first interior space 504 is fluidized to form the fluidized powder mixture and only the powdered agent within the first interior space 504 is permitted to exit the device 500 to the target site.

The second interior space 550 may be in communication with the first interior space 504 via an opening 554 extending therebetween. The device 500 further comprises a door 558 movable between a first configuration prior to commencement of a treatment procedure, as shown in FIG. 8, and a second configuration during a course of treatment, as shown in FIG. 9. In the first configuration, the door 558 may extend over the entire opening 554 when fluidized powder mixture is not being delivered, to prevent the passage of any powdered agent from the second interior space 550 to the first interior space 504. As shown via the dotted line in FIG. 8, the first interior space 504 contains a given volume of powdered agent therein.

When the user actuates and/or triggers delivery of the fluidized powder mixture, as shown in FIG. 9, movement of the door 558 may also be triggered so that the door 558 opens to expose the opening 554, permitting the passage of powdered agent from the second interior space 550 to the first interior space 504. Actuation of the door 558 may be triggered in any of a number of different ways. For example, the door 558 may include a motor that is activation, upon actuation of the device 500, a magnetic mechanism that uses magnetism to open the door 558 upon activation and/or pressure differentials created by the pressure increase upon device actuation. The second interior space 550 may include an angled surface 560 which directs the powdered agent toward the opening 554 so that, when the door 558 is open, the powdered agent within the second interior space 550 is permitted to fall into the first interior space 504. Thus, the first interior space 504 is passively fed with the additional powdered agent via gravity. As shown via the dotted line in FIG. 9, the volume of powder within the first interior space 504 should remain constant during the course of treatment since the first interior space 504 is being fed via the second interior space 550 as the fluidized powder mixture is being delivered. The opening 554 may be sized and/or otherwise configured to allow powdered agent to fall therethrough at a controlled rate selected to keep the volume of powdered agent within the first interior space 504 substantially constant.

Figure 11:
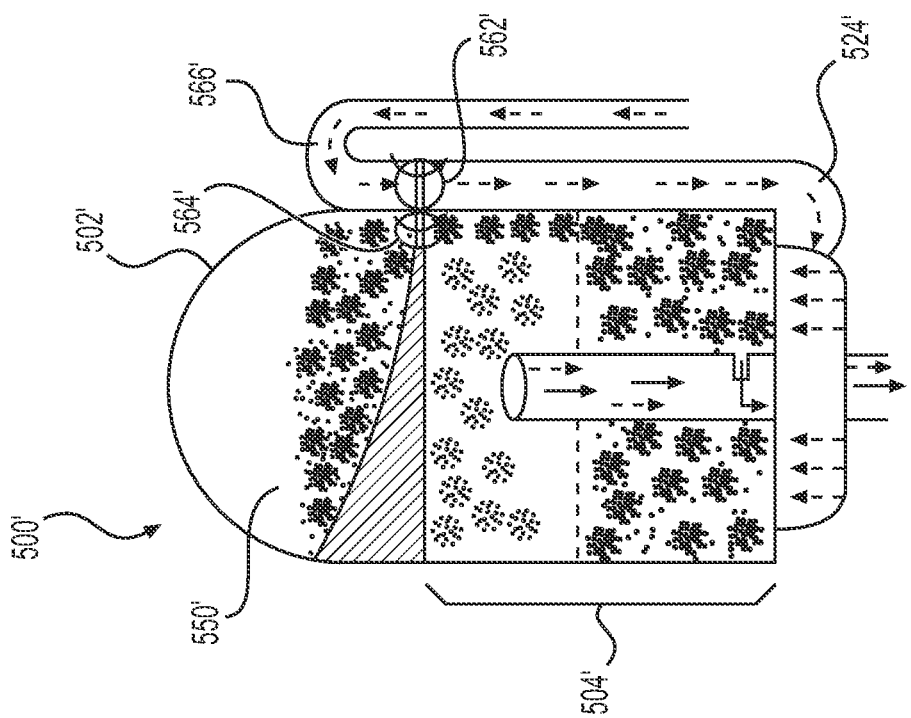
FIG. 11 shows a schematic view of the device of FIG. 10, in a second configuration.
Figure 10:
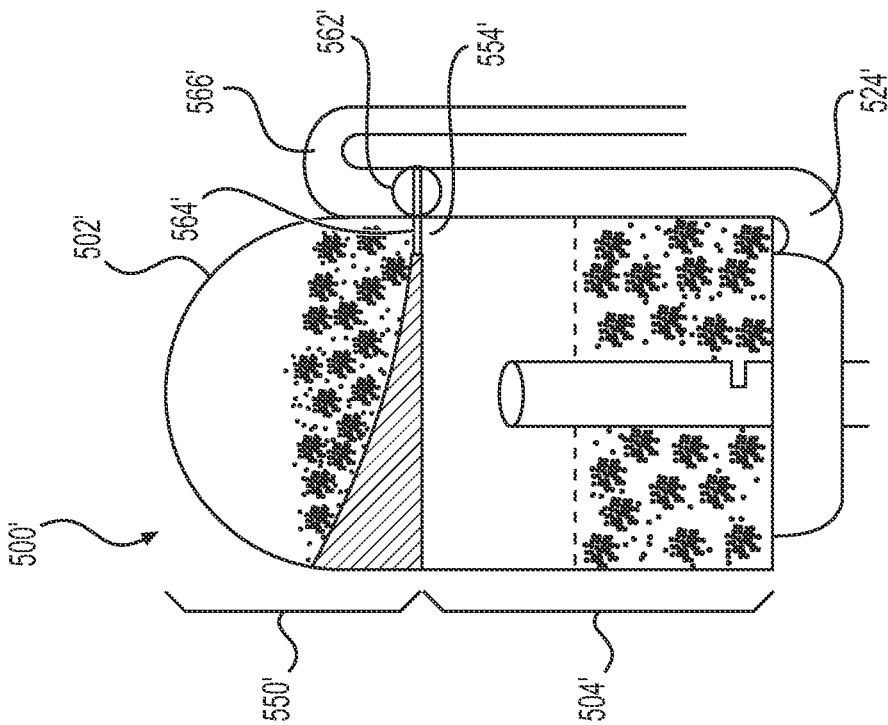
FIG. 10 shows a schematic view of a device according to an alternate embodiment of the present disclosure, in a first configuration.

Although the additional powdered agent within the second interior space 550 is described as being passively fed into the first interior space 504 via gravity, in an alternate embodiment, as shown in FIGS. 10 and 11, powdered agent within a second interior space 550' of a canister 502' of a device 500' may be actively fed into a first interior space 504' of the canister 502' via, for example, a turbine 562' which may be powered via a gas flow. In this embodiment, a rotatable paddle 564' is mounted within an opening 554' extending between the first and second interior spaces 504', 550'. The rotatable paddle 564' is connected to the turbine 562', which is positioned along an exterior of the canister 502' and housed within a gas flow path 566'. The gas flow path 566' may be configured as a connecting element 524' connecting a gas source to an inlet (not shown), which permits passage of gas therethrough into the first interior space 504. Thus, the connecting element 524', in this embodiment, extends along an exterior side of the canister 502' to accommodate the turbine 562'.

In a first configuration of device 500', as shown in FIG. 10, in which delivery of fluidized powder mixture is not actuated and thus no gas flows through the flow path 566', the turbine 562' does not rotate and thus no powdered agent is permitted to pass from the second interior space 550' to the first interior space 504'. As shown in FIG. 11, when delivery of the fluidized powder mixture is actuated, in a second configuration, the turbine 562' is rotated via a flow of gas passing through the gas flow path 566'. Rotation of the turbine 562' correspondingly rotates the paddle 564' to actively drive the powdered agent within the second interior space 550' through the opening 554' and into the first interior space 504'. Since the flow of gas is initiated when a user actuates and/or otherwise triggers delivery of a fluidized powder mixture to a target site, a supply of powdered agent from the second interior space 550' to the first interior space 504' will occur simultaneously with the exiting of powdered agent (e.g., the fluidized powder mixture) from the first interior space 504' to maintain a substantially constant volume of powdered agent within the first interior space 504'. Maintaining the volume of powdered agent within the first interior space 504' will correspondingly maintain a substantially constant delivery rate of the fluidized powder mixture.

Although the above embodiment describes a single gas source/supply, it will be understood by those of skill in the art that the turbine 562' may be driven via a gas source separate from a gas source connected to an inlet of the device 500' so long as a volume of powdered agent supplied from the second interior space 550' to the first interior space 504' corresponds to a volume of powdered agent exiting the first interior space 504'. In addition, although the embodiment describes active transfer of the powdered agent via a gas powered turbine, active transfer from the second interior space 550' to the first interior space 504' may also occur via other mechanisms.

As shown in FIG. 12, a device 1200 for fluidizing and delivering a powdered agent (e.g., hemostatic agent) according to an embodiment of the present disclosure comprises a canister 1202 and a piston 1204 movably coupled to the canister 1202. The canister 1202 is configured to receive the powdered agent within an interior space 1206 thereof. The canister 1202 is subsequently filled with a gas via an inlet 1208 that may be connected to a gas source via, for example, a tubular member 1212. The powder is fluidized via the gas to form a two-phase mixture that may be sprayed onto the target site (e.g., bleeding site) via a catheter 1214 connected to an outlet 1210. The catheter 1214 is sized and shaped and sufficiently flexible to be endoscopically inserted into a patient body to the target site (e.g., along a tortuous path traversed by a flexible endoscope through a body lumen accessed via a natural body orifice). In order to maintain a substantially constant delivery rate of the mixture to the target site, the piston 1204 is movable relative to the canister 1202 to decrease a volume of the interior space 1206, during the course of treatment of the target site. Thus, as a volume of powder within the canister 1202 is decreased, the volume of the interior space 1206 is also decreased to maintain a substantially constant powder volume to canister volume ratio. The piston 1204 may be moved relative to the canister 1202 in any of a number of different ways. In this embodiment, the piston 1204 is moved via a pneumatic cylinder or motor 1220.

The canister 1202 of this embodiment is formed of a rigid material to define the interior space 1206, which is configured to receive the powdered agent along with the gas to form the gaseous fluid mixture that is sprayed on the target site to provide treatment thereto. The canister 1202 extends longitudinally from an open first end 1216 to a closed second end 1218. The piston 1204 is movably coupled to the canister 1202 at the first end 1216 and is movable toward the second end 1218 to reduce the volume of the interior space 1206. The piston 1204 encloses the interior space 1206 so that the powder, gas and/or the gas mixture do not leak from the canister 1202, and exit the canister 1202 via the outlet 1210 and from there into the catheter 1214 to exit toward the target site. Thus, the piston 1204 of this embodiment is received within the open first end 1216 and is substantially sized and shaped to correspond to a size and shape of an opening at the first end 1216. In one example, the canister 1202 is substantially cylindrical while the piston 1204 is substantially disc-shaped to be received within the open first end 1216 of the canister 1202. The canister 1202 is sized and shaped so that the piston 1204 is movable along at least a portion of a length thereof toward the second end 1218 to reduce a volume of the interior space 1206 while also preventing leakage of any fluids/substances received within the interior space 1206. In one example, the piston 1204 includes a sealing ring extending about a circumference thereof to prevent leakage of any powder, gas and/or fluid therepast.

As described above, the device 1200 also includes the inlet 1208 via which gas is introduced into the interior space 1206 and the outlet 1210 via which the fluidized powder is delivered to the catheter 1214 to reach the target site. In one embodiment, each of the inlet 1208 and the outlet 1210 are configured as an opening extending through a portion of the piston 1204 to be connected to the tubular member 1212 and the catheter 1214, respectively. It will be understood by those of skill in the art, however, that the inlet 1208 and the outlet 1210 may be positioned on or along any portion of the canister 1202 and/or the piston 1204 so long as the inlet 1208 is configured to receive a high pressure gas therethrough and into the interior space 1206, and the outlet 1210 is connectable to a delivery element such as, for example, the catheter 1214, which delivers the fluidized mixture from the interior space 1206 to the target site. It will also be understood by those of skill in the art, that although the inlet 1208 is described as connected to the gas source via the tubular member 1212, the inlet 1208 may be connected to the gas source via any of a number of couplings so long as sufficient gas flow is deliverable therethrough. In addition, although the outlet 1210 is shown and described as an opening extending through the piston 1204, it will be understood by those of skill in the art that the outlet 1210 may also be configured to include a hypotube extending into the interior space 1206 so that fluidized mixture formed within the interior space 1206 may be received within the hypotube to be delivered to the target site via the catheter 1214.

In this embodiment, the piston 1204 is movable relative to the canister 1202 via a pneumatic cylinder or motor 1220. The device 1200 may be programmed to include one or more inputs such as, for example, time. When it is desired to deliver the fluidized mixture to the target site, the user may initiate delivery using a controller such as a trigger. For example, when the user depresses the trigger to deliver the fluidized mixture, the piston 1204 moves toward the second end 1218 at a preset rate. When the user releases the trigger, the piston 1204 may stop, maintaining its position relative to the canister 1202 until the user depresses the trigger again. Alternatively or in addition, the device 1200 may use other inputs such as, for example, inputs based on flow and/or pressure sensors within the interior space 1206 of the canister 1202, the inlet 1208 and/or the outlet 1210.

Although the piston 1204 of the device 1200 is described and shown as driven via the pneumatic cylinder or motor 1220, it will be understood by those of skill in the art that the piston 1204 may be moved from its initial position proximate the first end 1216 toward the second end 1218 via any of a variety of different drive mechanisms, examples of which will be described in further detail below. In addition, although the piston 1204 is shown as forming a base (e.g., bottom portion) of the canister 1202, it will be understood by those of skill in the art that the piston 1204 may be coupled to the canister 1202 in any of a number of configurations. In particular, the piston 1204 may also be configured as a lid (e.g., top portion) of the canister 1202. In a further embodiment, the device 1200 may include more than one piston 1204, each of which are movable relative to the canister 1202 to reduce the volume of the interior space 1206 thereof.

According to example method using the device 1200, the canister 1202 may be filled with the powdered agent such as, for example, a hemostatic agent, prior to assembly of the device 1200. Upon filling the canister 1202 with a desired amount of powder, the canister 1202 and the piston 1204 are assembled, the inlet 1208 is coupled to the gas source via, for example, the tubular member 1212, and the outlet 1210 is coupled to the catheter 1214. The catheter 1214 may then be inserted to the target site within the body through a working channel of a delivery device such as an endoscope. The user may depress a trigger or other controller to introduce a high flow gas into the interior space 1206 of the canister 1202 to form the fluidized mixture and deliver the fluidized mixture to the target site (e.g., a bleeding site) to provide treatment thereto. When the trigger is depressed, the pneumatic cylinder or motor 1220 is operated to move the piston 1204 toward the second end 1218 reducing the volume of the interior space 1206 by an amount corresponding to the reduction in the volume of powder remaining within the interior space 1206 as reduced the powder exits the canister 1202 via the outlet 1210. When the user releases the trigger, both the delivery of the fluidized mixture and the movement of the piston 1204 are halted. Thus, the piston 1204 moves only while the fluidized mixture is being delivered so the reduction in the volume of the interior space 1206 corresponds to the reduction in the volume of powder remaining housed within the interior space 1206. As described above, a rate of movement of the piston 1204 may be based on inputs such as, for example, time, flow and/or pressure within the canister 1202, inlet 1208 and outlet 1210. In one embodiment, the piston 1204 is configured to move at a rate which maintains a substantially constant ratio of the volume of the interior space 1206 available in the canister 1202 to the volume of remaining powder to maintain a substantially constant fluidized mixture delivery rate.

As shown in FIG. 13, a device 1300 according to another embodiment is substantially similar to the device 1200, comprising a canister 1302 and a piston 1304 movably coupled thereto to move from an initial position proximate a first end 1316 of the canister 1302 toward a second end 1318 to reduce a volume of an interior space 1306 of the canister 1302 as a fluidized powder mixture is delivered to a target site. Similarly to the device 1200, high flow gas is delivered to the interior space 1306 to fluidize a powdered agent received within the canister 1302 to form a fluidized mixture for delivery to a target site in the body. Gas is received within the canister 1302 via an inlet 1308 connected to a gas source via, for example, a tubular member 1312. The fluidized mixture is delivered to the target site via a delivery catheter 1314 connected to an outlet 1310 of the device 1300. In this embodiment, however, the piston 1304 is moved via a chamber 1320 including an expandable member 1322, which expands as gas is received therein. In particular, when a user triggers a controller (e.g., depresses a trigger) to deliver the fluidized mixture to the target site, a portion of the gas is diverted into the expandable member 1322 so that the gas expands the expandable member 1322, as shown in broken lines in FIG. 13, thereby moving the piston 1304 toward the second end 1318.

The chamber 1320, which houses the expandable member 1322, in this embodiment is connected to the first end 1316 of the canister 1302 on a side of the piston 1304 opposite the interior space 1306 so that, as the expandable member 1322 expands, the piston 1304 is moved toward the second end 1318 of the canister 1302. The expandable member 1322 is also connected to the gas source via a connecting member 1324, which includes a one way valve so that gas may pass therethrough in a first direction into the expandable chamber 1322, but is prevented from flowing in a second direction out of the expandable chamber 1322. As described above, gas is directed into the chamber 1320 only while the fluidized mixture is being delivered to the target site so that a reduction of the volume of the interior space 1306 corresponds to a reduction in volume of the powdered agent within the canister 1302. Similarly to the device 1200, the device 1300 may receive inputs corresponding to flow, pressure and/or time, that may control a rate at which the piston 1304 is moved toward the second end 1318. It will be understood by those of skill in the art that the device 1300 may be used in a manner substantially similar to the device 1200.

Figure 15:
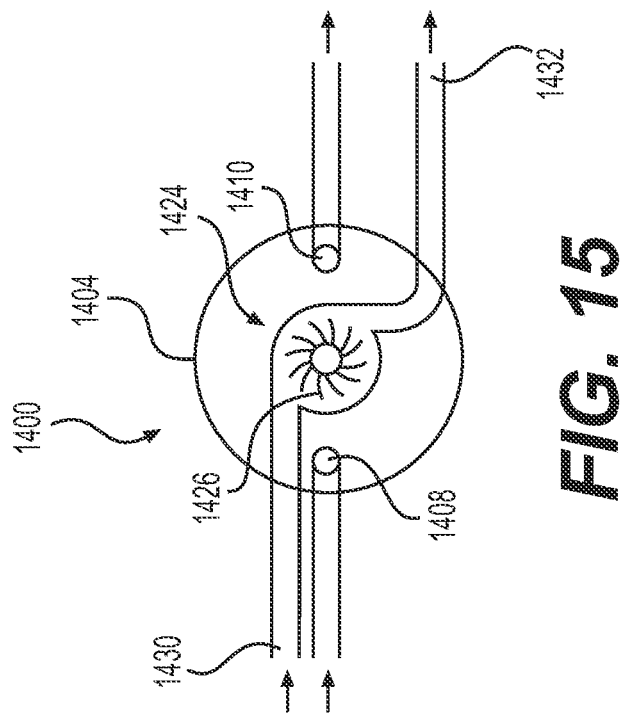
FIG. 15 shows a bottom view of the device according to FIG. 14.
Figure 14:
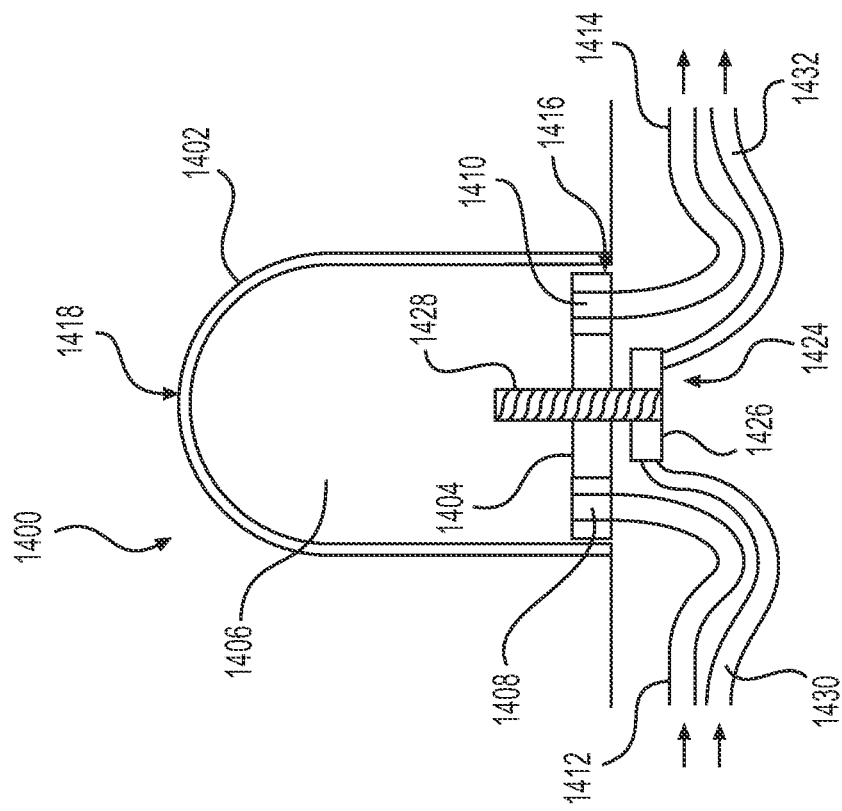
FIG. 14 shows a schematic view of a device according to another alternate embodiment of the present disclosure.

As shown in FIGS. 14 and 15, a device 1400 according to another embodiment may be substantially similar to the devices 1200 and 1300 described above, comprising a canister 1402 for receiving a powdered agent within an interior space 1406 thereof and a piston 1404 movably coupled to the canister 1402. High flow gas is delivered to the interior space 1406 via an inlet 1408 that is connected to a gas source to form a fluidized powder mixture for delivery to a target treatment area via a delivery catheter 1414 connected to an outlet 1410 of the device 1400. The piston 1404 is movable from an initial position proximate a first end 1416 of the canister 1402 toward a second end 1418 to reduce a volume of the interior space 1406 as a volume of the powdered agent within the interior space 1406 is reduced. The device 1400, however, further includes a turbine 1426 connected to a threaded rod 1428 to which the piston 1404 is threadedly coupled. The turbine 1426 is housed within a bypass 1424 connected to the first end 1416 if the canister 1402. A portion of the gas is diverted through the bypass 1424 when the user triggers a controller to deliver the fluidized mixture. The flow of gas through the bypass 1424 spins the turbine 1426, thereby causing the threaded rod 1428 to rotate about a longitudinal axis thereof. As the threaded rod 1428 is rotated, the piston 1404 is moved longitudinally therealong toward the second end 1418.

As shown in FIG. 15, the bypass 1424 including a first opening 1430 through which gas is received and second opening 1432 through which gas exits so that gas flows through the bypass 1424 from the first opening 1430 to the second opening 1432 to rotate the turbine 1426 housed therein. The threaded rod 1428 is connected to the turbine 1426 so that rotation of the turbine 1426 results in rotation of the threaded rod 1428. Since the piston 1404 is threaded over the rod 1428, rotation of the threaded rod 1428 causes the piston 1404 to be moved longitudinally therealong. The piston 1404 is threaded over rod 1428 so that rotation of the threaded rod 1428 via the flow of gas through the bypass 1424 results in the longitudinal movement of the piston 1404 toward the second end 1418. Similarly to the device 1300, a portion of the gas is only diverted through the bypass 1424 during delivery of the fluidized mixture so that a reduction in volume of the interior space corresponds to a volume of powder remaining in the interior space 1406. It will be understood by those of skill in the art that the device 1400 may be used in a manner substantially similar to the devices 1200, 1300, as described above.

Figure 16:
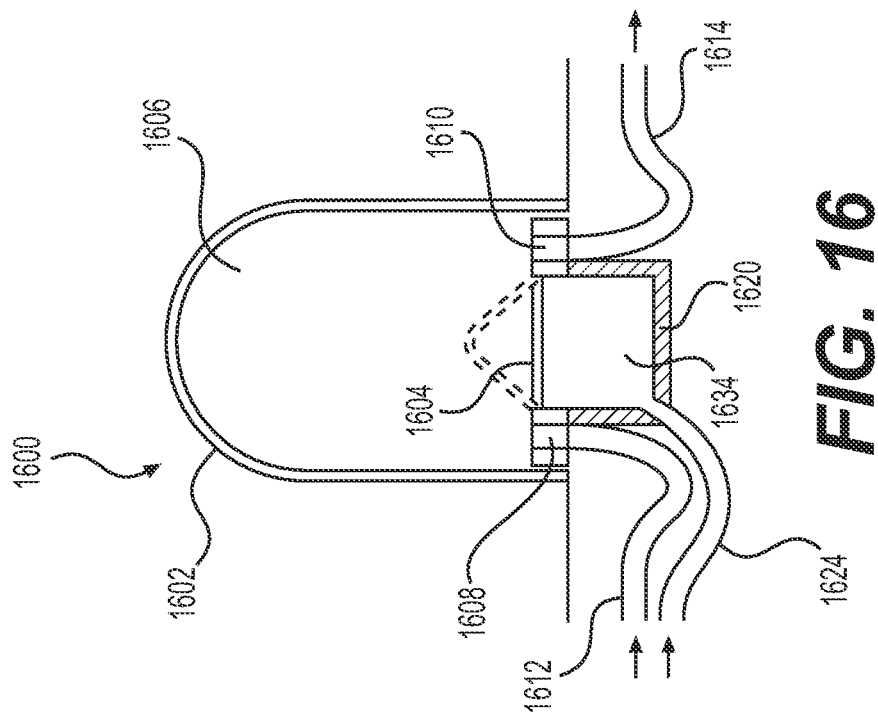
FIG. 16 shows a schematic view of a device according to another embodiment of the present disclosure.

As shown in FIG. 16, a device 1600 according to another embodiment of the present disclosure may be substantially similar to the devices 1200, 1300, and 1400, described above, comprising a canister 1602 configured to receive a powdered agent therein for fluidization via a gas. Similar to the devices 1200, 1300, and 1400, a volume of an interior space 1606 of the canister 1602 is reduced as a fluidized mixture is delivered to a target site for treatment. Rather than reducing the volume of the interior space 1606 via a movable piston, however, the device 1600 includes an expandable member 1604 which expands into the interior space 1606, as shown in broken lines in FIG. 16, of the canister 1602 to reduce the volume thereof.

Similarly to the devices 1200, 1300, and 1400, gas is supplied into the canister 1602 via an inlet 1608, which may be connected to a gas source via a connecting member 1612. The fluidized mixture is delivered to the target site via a delivery catheter 1614 connected to an outlet 1610. The device 1600 further comprises a secondary chamber 1620 connected to the canister 1602. Similarly to the device 1300 described above, a portion of the gas from the gas source may be diverted into the secondary chamber 1620 during delivery of the fluidized mixture. An interior space 1634 of the secondary chamber 1620 is separated from the interior space 1606 of the canister 1602 via the expandable member 1604. In this embodiment, the expandable member 1604 is configured as an expandable diaphragm extending between the canister 1602 and the secondary chamber 1620 so that, when gas is received within the interior space 1634 of the secondary chamber 1620 via feed tube 1624, a pressure differential between the interior space 1634 of the secondary chamber 1620 and the interior space 1606 of the canister 1602 causes the expandable member to deflect into the canister 1602, as shown in broken lines in FIG. 16 reducing the volume of the interior space 1606.

As described above with respect to the devices 1300, 1400, gas is only diverted into the secondary chamber 1620 during the delivery of the fluidized mixture. When delivery is triggered gas is diverted to the secondary chamber 1620. When the user releases the trigger for delivery, delivery of gas to the secondary chamber 1620 is halted. As also discussed above, the amount of flow diverted to the secondary chamber 1620 may be dictated by time, pressure and/or flow detected within the device 1600. As more gas flows into the secondary chamber 1620, its pressure increases to force the diaphragm to deflect further into the interior space 1606 of the canister 1602. Thus, the device 1600 may be utilized in a manner substantially similar to the devices described above.

Although the device 1600 shows and is described with respect to a single expandable diaphragm, it will be understood by those of skill in the art that the device 1600 may include more than one expandable diaphragm and the expandable member may have any of a variety of shapes and configurations.

Figure 17:
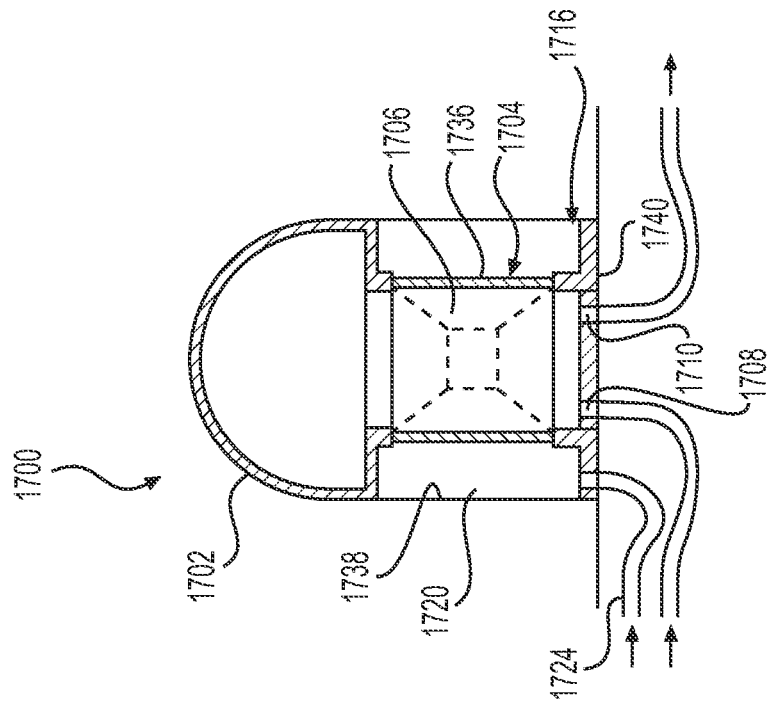
FIG. 17 shows a schematic view of a device according to yet another embodiment of the present disclosure.

As shown in FIG. 17, a device 1700 according to another embodiment may be substantially similar to the device 1600, described above, comprising a canister 1702 including an expandable member 1704 which expands to reduce a volume of a first interior space 1706 of the canister 1702 as a powdered agent received therewithin is fluidized and delivered to a target site for treatment. In this embodiment, however, the expandable member 1704 may be housed within the canister 1702 to define both the first interior space 1706 in which the powdered agent is fluidized and a second interior space 1720 into which a portion of a gas may be diverted to cause the expandable member 1704 to deflect into the first interior space 1706 to reduce a volume thereof. A first end 1716 of the canister 1702 may be substantially closed via a base portion 1740. An inlet 1708 for supplying gas into the first interior space 1706 and an outlet 1710 via which the fluidized mixture is delivered to the target site may extend through the base portion 1740 in communication with the first interior space 1706.

The expandable member 1704 may, in one example, have a substantially cylindrical configuration. The cylindrically shaped expandable member 1704 is housed within the canister 1702 so that an interior of the expandable member 1704 defines the first interior space 1706 within which the powdered agent is housed and subsequently fluidized via a high flow gas supplied from a gas source thereto via the inlet 1708. The second interior space 1720 is defined via an exterior surface 1736 of the expandable member 1704 and an interior surface 1738 of the canister 1702 so as the fluidized mixture is delivered to the target site from the first interior space 1706 via a delivery catheter 1714 connected to the outlet 1710, a portion of gas from the gas source gas is diverted into the second interior space 1720 via a connecting element 1724. A pressure differential between the first and second interior spaces 1706, 1720 causes the expandable member 1704 to deflect into the first interior space 1706, as shown in broken lines in FIG. 17, toward an expanded configuration, as shown via the broken lines in FIG. 17, reducing the volume of the first interior space 1706 as a volume of the powder in the first interior space 1706 is reduced. In one embodiment, in the expanded configuration, the expandable member 1704 may form a substantially hourglass shape. It will be understood by those of skill in the art, however, that the expandable member 1704 may have any of a variety of shapes and configurations so long as the expandable member 1704, when expanded, reduces a volume of the first interior space 1706. Similarly to the devices described above, gas is only diverted into the second interior space 1720 during delivery of the fluidized mixture and may be controlled via inputs including time, and/or flow and/or pressure within the device 1700.

Although the device 1700 is shown and described as including a substantially cylindrically shaped expandable member 1704, it will be understood by those of skill in the art that the expandable member 1704 may have any of a variety of shapes so long as the expandable member defines first and second interior spaces 1706, 1720, as described above.

Figure 18:
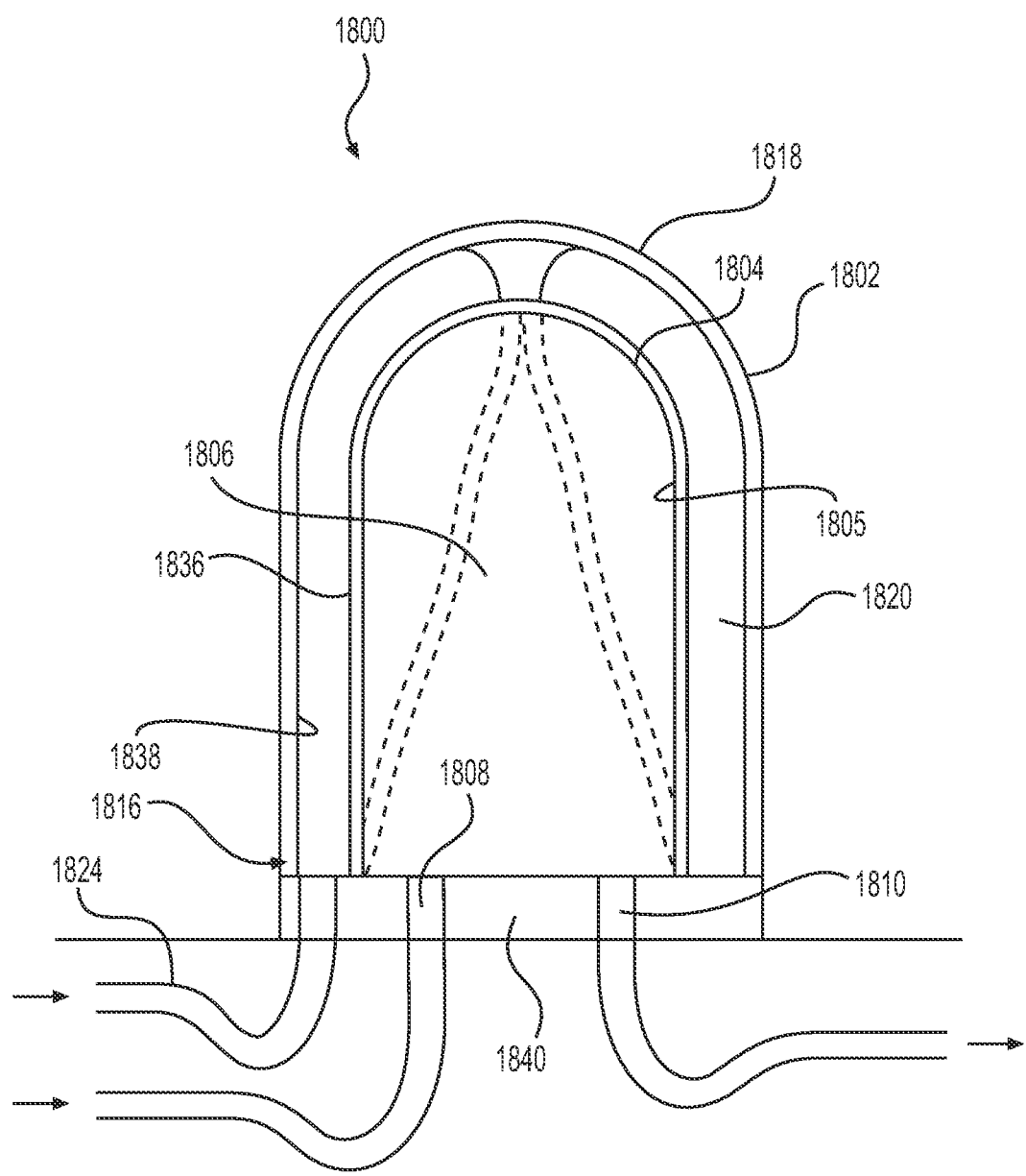
FIG. 18 shows a schematic view of a device according to another embodiment.
Figure 20:
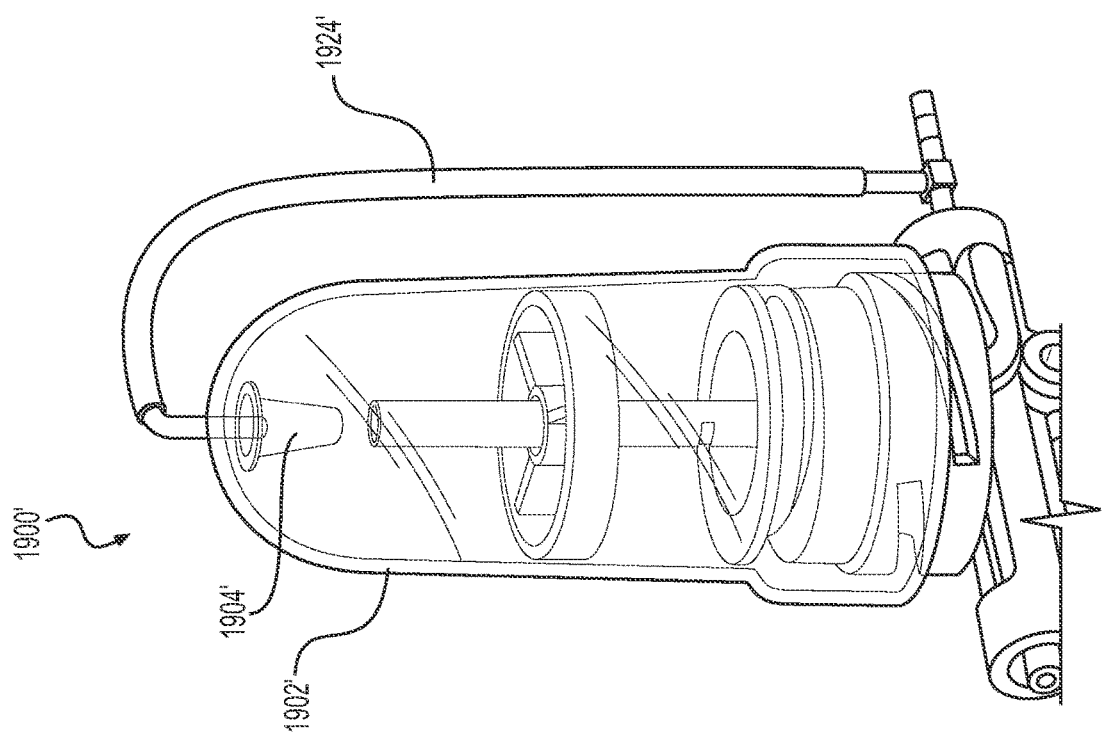
FIG. 20 shows a schematic view of a device according to an alternate of the present disclosure.

As shown in FIG. 18, a device 1800 according to another embodiment may be substantially similar to the device 1700 described above, comprising a canister 1802 and an expandable member 1804 defining a first interior space 1806, in which a powdered agent is fluidized via gas from a gas source to form a fluidized mixture, and a second interior space 1820, which receives a portion of gas diverted from the gas source during delivery of the fluidized mixture to a target treatment area. The first interior space 1806 is defined via an interior wall 1805 of the expandable member 1804. The second exterior space 1820 is defined via an exterior wall 1836 of the expandable member 1806 and the interior surface 1838 of the canister 1802. In this embodiment, however, the expandable member 1804 extends from a first end 1816 of the canister 1802 to a second end 1818 of the canister 1802 so that, in an initial biased configuration, the expandable member 1804 may substantially correspond in shape to the canister 1802. As the second interior space 1820 is filled with diverted gas, however, the expandable member 1804 deflects into the first interior space 1806, as shown in broken lines in FIG. 18, increasing a volume of the second interior space 1820 and thereby reducing a volume of the second interior space 1820.

Similarly to the device 1700, the device 1800 also includes a base portion 1840 at a first end 1816 of the canister 1802 for enclosing the first and second interior spaces 1806, 1820. An inlet 1808 and an outlet 1810 extend through the base portion 1840 in communication with the first interior space 1806 so that gas may be supplied thereto via the inlet 1808 to fluidize the powdered agent therein and so that the fluidized mixture may be delivered to the target site via the outlet 1810. A portion of the gas from the gas source may be diverted into the second interior space 1820 via a connecting element 1824, which may be positioned along the base portion 1840 in communication with the second interior space 1820.

As described above, during delivery of the fluidized mixture to the target site, a portion of the gas is diverted into the second interior space 1820 so that a pressure differential between the first and second interior spaces 1806, 1820 causes the expandable member to be diverted radially inward, as shown in broken-lines in FIG. 18, to reduce the volume of the first interior space 1806. Thus, as the volume of the powdered agent within the first interior space 1806 is reduced, the volume of the first interior space 1806 is correspondingly reduced to maintain a substantially constant delivery rate of the fluidized mixture. In a diverted configuration, the expandable member 1804 may take on a substantially conical shape. It will be understood by those of skill in the art, however, that the expandable member 1804 may have any of a configurations, shapes and sizes so long as the expandable member 1804 is formed of a flexible, deflectable material which defines both a first interior space 1806 within walls thereof, and a second interior space 1820 between the expandable member 1804 and walls of the canister 1802.

Figure 19:
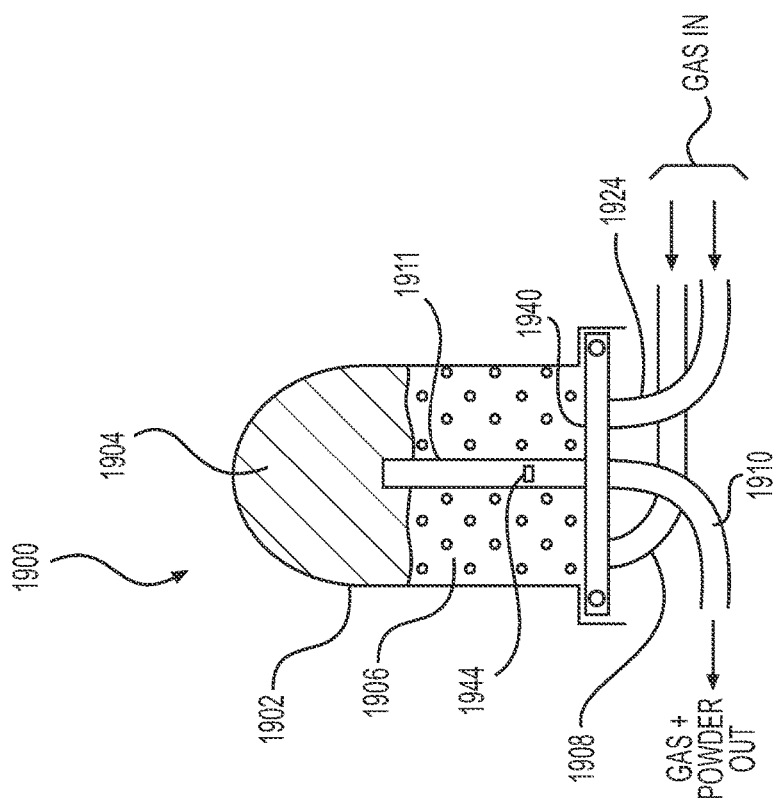
FIG. 19 shows a schematic view of device according to yet another embodiment of the present disclosure.

As shown in FIG. 19, a device 1900 according to another embodiment may be substantially similar to the devices 1600, 1700, and 1800 described above, comprising a canister 1902 and an expandable member 1904, which expands to reduce a volume of an interior space 1906 of the canister 1902 as a powdered agent is fluidized and delivered to a target site of treatment. The volume of the interior space 1906 is reduced to correspond to a reduction in a volume of the powdered agent within the interior space 1906. The expandable member 1904 in this embodiment, however, is configured as an expandable balloon housed within the interior space 1906. Thus, as a volume of the balloon 1904 is increased as it is inflated, the volume of the interior space 1906 is decreased.

Similarly to the devices 1600, 1700, and 1800, the device 1900 includes an inlet 1908 for supplying a gas to the interior space 1906 to fluidize the powdered agent and an outlet 1910 via the fluidized mixture is delivered to the target site. The inlet and outlet 1908, 1910, respectively, may extend through a base portion 1940 of the device 1900 which is coupled to an end of the canister 1902 to define the interior space 1906. A portion of the gas supplied to the device 1900 may be diverted to the expandable member 1904 via a connecting element 1924 to cause the balloon to become inflated, filling the interior space 1906. As described above, the inlet 1908 may have any of a variety of configurations and, in one embodiment, may include a hypotube 1911 extending into the interior space 1906. The hypotube 1911 may include a slot 1944 extending through a wall thereof along a portion thereof. The inflated expandable member 1904 may fill the space, surrounding the hypotube 1911 without restricting gas and powder flow through the slot 1944. Although the hypotube 1911 is described as including the slot 1944, it will be understood by those of skill in the art that the term "slot" may refer to any opening or hole extending through a wall thereof.

The connecting element 1924 may be coupled to the base portion 1940, as shown, to deliver gas to the expandable member 1904. It will be understood by those of skill in the embodiment, that the connecting element 1920 may extend through the interior space 1906 to connect to the expandable member 1904. Alternatively, as shown in FIG. 20, a device 1900' may have a separate feed line 1924' which extends through a portion of a canister 1902' to supply gas to an expandable member 1904' housed therein. It will be understood by those of skill in the art that an expandable member 1904, 1904' having a balloon configuration may be supplied with gas for inflating the expandable member via any of a variety of mechanisms.

Although the above embodiments are described as diverting a portion of gas from a gas source/supply to drive movement of a piston or expansion of an expandable member, it will be understood by those of skill in the art that the devices described above may include one or more gas source(s) for providing gas to both the interior space and for driving the piston and/or causing expansion of the expandable member.

It will be apparent to those skilled in the art that various modifications and variations can be made to the disclosed device without departing from the scope of the disclosure. For example, various other structures and techniques for maintaining a consistent output of material from a dispensing device to a target site may be achieved. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for delivering a powdered agent, comprising:
a canister extending longitudinally from a first end to a second end, the canister defining an interior space configured to store the powdered agent;
an inlet fluidly coupled to a fluid source for supplying pressurized fluid towards the canister for delivering the powdered agent from the device;

an outlet configured to direct a mixture of the powdered agent and the pressurized fluid out of the device; and a piston movably coupled to the canister and disposed between the powdered agent stored in the interior space and the outlet, the piston is configured to move within the canister relative to the first end and the second end to move the powdered agent out of the interior space and towards the outlet.

2. The device of claim 1, wherein each of the inlet and the outlet is in fluid communication with the piston, such that the pressurized fluid from the inlet enters the canister through the piston and the mixture of the powdered agent and the pressurized fluid exits the canister for delivery to the outlet through the piston.

3. The device of claim 1, wherein at least one of the first end and the second end of the canister is open to receive the piston within the interior space of the canister.

4. The device of claim 1, wherein the fluid source includes a pneumatic cylinder configured to store the pressurized fluid.

5. The device of claim 4, wherein the piston is configured to translate relative to the canister in response to the pneumatic cylinder releasing the pressurized fluid through the inlet and towards the piston.

6. The device of claim 1, wherein the piston is configured to translate relative to the canister to a position that seals the interior space, thereby preventing the powdered agent from exiting the canister.

7. The device of claim 1, wherein the device is configured to initiate delivery of the pressurized fluid from the fluid source to the inlet prior to supplying the pressurized fluid towards the canister.

8. The device of claim 7, wherein the device is configured to move the piston relative to the canister in response to initiating delivery of the pressurized fluid from the fluid source to the inlet.

9. The device of claim 1, further comprising a chamber positioned along a side of the piston.

10. The device of claim 9, wherein the chamber is configured to receive at least a portion of the pressurized fluid therein.

11. The device of claim 1, further comprising a turbine coupled to the piston.

12. The device of claim 11, wherein the turbine is configured to move with the piston in response to the inlet supplying the pressurized fluid from the fluid source towards the turbine.

13. The device of claim 12, wherein the turbine is configured to rotate relative to the canister in response to receiving a flow of the pressurized fluid from the inlet.

14. The device of claim 13, wherein the turbine is configured to deliver the powdered agent towards the outlet in response to the turbine rotating relative to the canister.

15. A device for delivering a powdered agent, comprising:
a canister including an interior space defined between a first end and a second end, the interior space configured to store the powdered agent;

a fluid source configured to store a pressurized fluid; and a piston movably coupled to the canister and disposed in the interior space between the powdered agent positioned adjacent to the first end and an outlet that is in fluid communication with the second end, the piston is configured to move relative to the first end and the second end to deliver the powdered agent out of the interior space.

16. The device of claim 15, wherein at least one of the first end and the second end of the canister is open to receive the piston within the interior space of the canister.

17. The device of claim 15, wherein the piston is configured to translate relative to the canister in response to the fluid source releasing the pressurized fluid towards the piston.

18. The device of claim 15, wherein the device is configured to initiate delivery of the pressurized fluid from the fluid source and move the piston relative to the canister initiating delivery of the pressurized fluid from the fluid source to the inlet.

19. The device of claim 15, further comprising a chamber positioned along a side of the piston that is configured to receive at least a portion of the pressurized fluid.

20. A device for delivering a powdered agent, comprising:

a canister including an interior space that is configured to store the powdered agent;

an inlet in fluid communication with a fluid source that is configured to store a pressurized fluid;

an outlet in fluid communication with the canister and the inlet to direct the powdered agent and the pressurized fluid out of the device; and a piston configured to move relative to the interior space of the canister to direct the powdered agent out of the interior space and towards the outlet, wherein the piston is disposed in the interior space between the powdered agent and the outlet such that the powdered agent is stored in the canister upstream from the powdered agent.

* * * * *